(12) United States Patent
Xu

(10) Patent No.: US 6,972,195 B2
(45) Date of Patent: Dec. 6, 2005

(54) COMPOSITION AND METHOD FOR CULTURING POTENTIALLY REGENERATIVE CELLS AND FUNCTIONAL TISSUE-ORGANS IN VITRO

(75) Inventor: Rongxiang Xu, Arcadia, CA (US)

(73) Assignee: Rongxiang Xu, Arcadia, CA (US)

( * ) Notice: Subject to any disclaimer, the term of this patent is extended or adjusted under 35 U.S.C. 154(b) by 31 days.

(21) Appl. No.: 10/335,143

(22) Filed: Dec. 31, 2002

(65) Prior Publication Data

US 2004/0063205 A1    Apr. 1, 2004

(30) Foreign Application Priority Data

Sep. 27, 2002  (CN) .............................. 02143546 A

(51) Int. Cl.[7] .............................. C12N 5/06; C12N 5/08
(52) U.S. Cl. ...................... 435/383; 435/384; 435/390; 435/391; 435/404; 435/375; 435/377
(58) Field of Search ................................ 435/375, 377, 435/383, 394, 390, 391, 404

(56) References Cited

U.S. PATENT DOCUMENTS

| | | |
|---|---|---|
| 5,372,943 A * | 12/1994 | Inlow et al. ................. 435/404 |
| 5,486,510 A * | 1/1996 | Bouic et al. ................. 514/170 |
| 5,552,148 A * | 9/1996 | Znaiden et al. ............. 424/401 |
| 5,853,755 A * | 12/1998 | Foldvari ..................... 424/450 |
| 6,833,271 B2 * | 12/2004 | Bertheussen ................ 435/404 |

OTHER PUBLICATIONS

Awad et al., FASEB Journal. (Mar. 7, 2001), vol. 15, No. 4, p. A599.*
Hoffman et al. Blood. (1981), vol. 57, No. 1, pp. 164-169.*
Bhadra et al. Incorporation of liposomal phytosterols into human cells in culture. Biochemical Medecine and Metabolic Biology. 1991. 46, pp. 119-124.*

* cited by examiner

Primary Examiner—Vera Afremova
(74) Attorney, Agent, or Firm—Shirley Chen; Wilson Sonsini Goodrich & Rosati

(57) ABSTRACT

Compositions and methods are provided for culturing in vitro potentially regenerative cells (PRCs) from which functional tissue-organs are regenerated. In one aspect of the invention, a tissue culture medium is provided which comprises at least 50% of water and a sterol compound that is dissolved in a fatty acid-containing oil at a concentration at least 0.1% by weight based on the weight of the oil and added to the water. The culture medium can be used to culture PRCs that are isolated from the body of a mammal to generate functional tissue-organs in vitro with substantially the same physiological structure and function as the corresponding ones existing in vivo and in situ. The cultured PRCs, tissues, and tissue-organs can serve as valuable models for scientific investigation in life sciences, nutraceutical discovery, drug screening, pharmacokinetic studies, medical devices and tissue/organ transplantation.

23 Claims, 31 Drawing Sheets

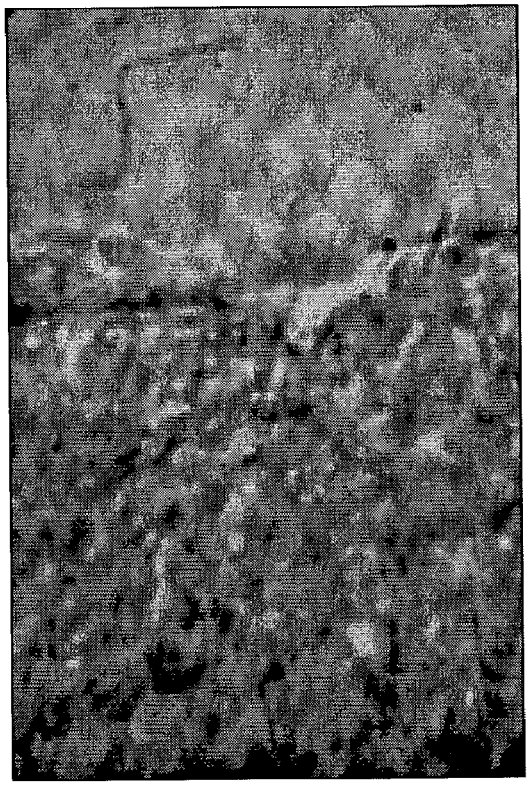
Control
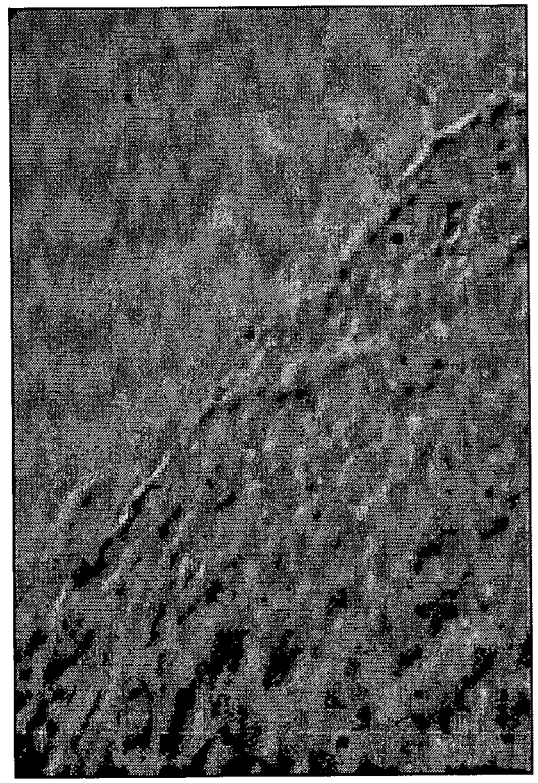
Test
FIGURE 6

Control
Test
FIGURE 7

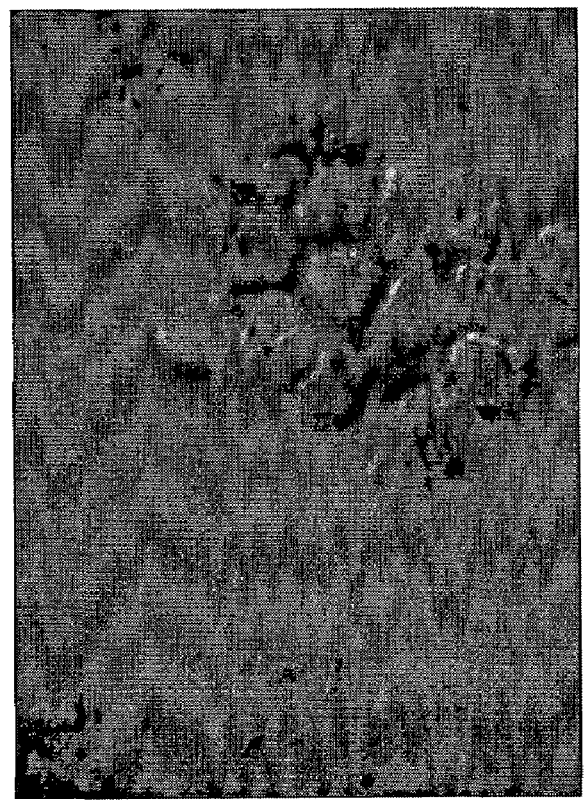
FIGURE 9

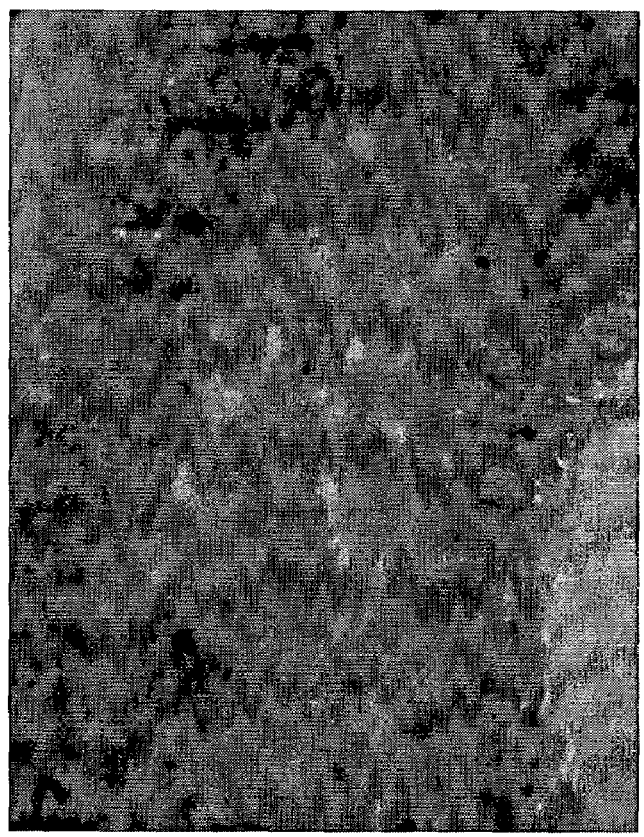
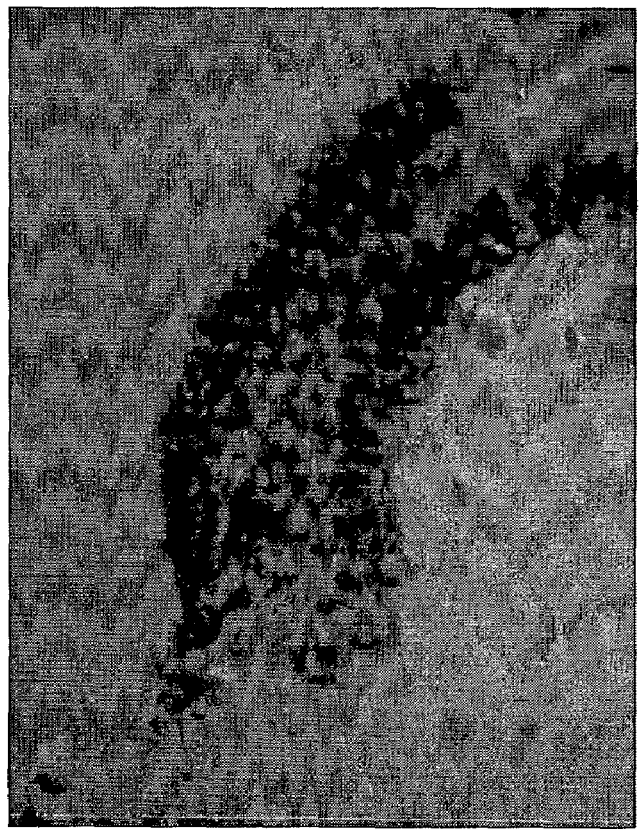
FIGURE 10

FIGURE 14

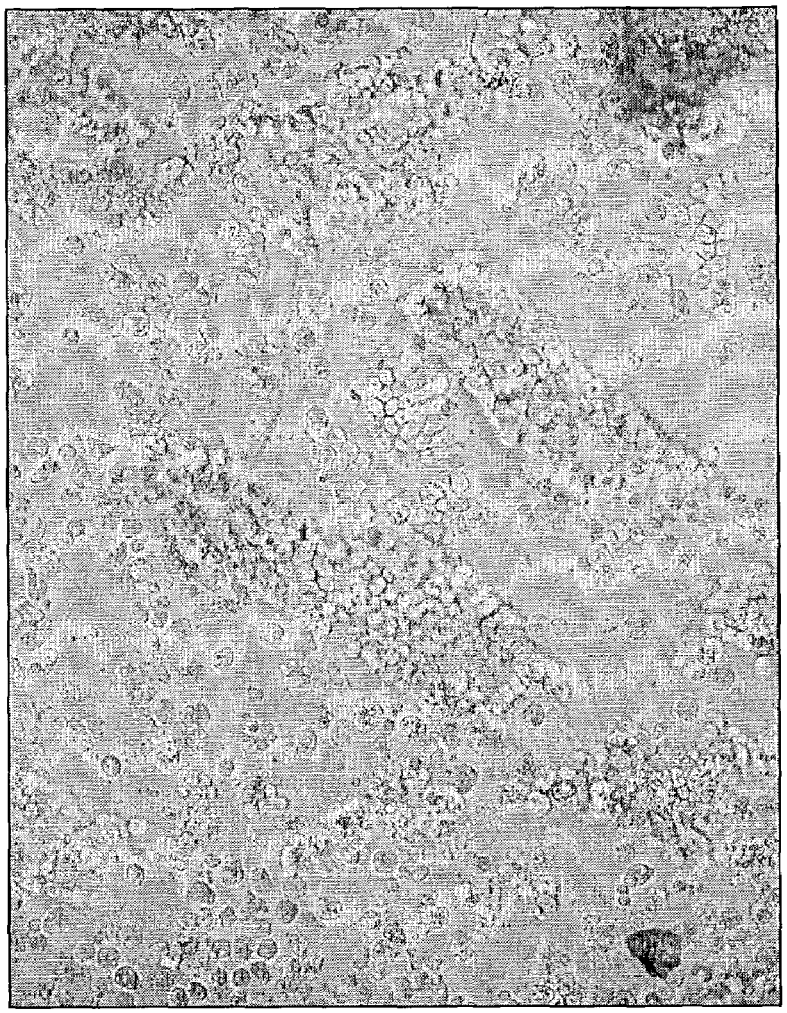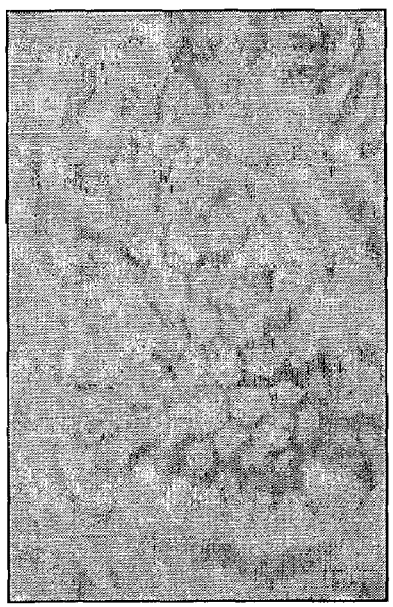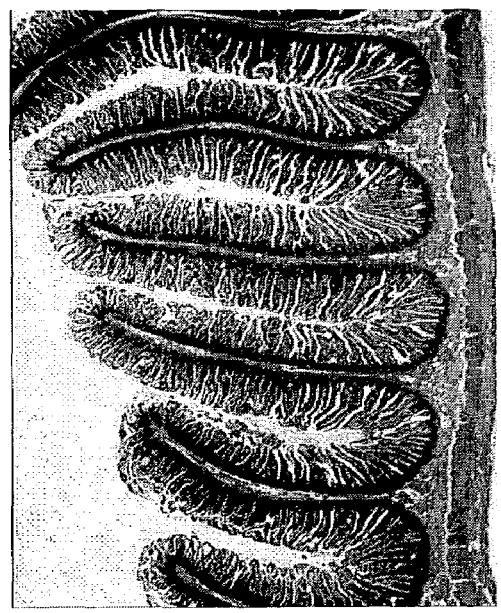
FIGURE 15

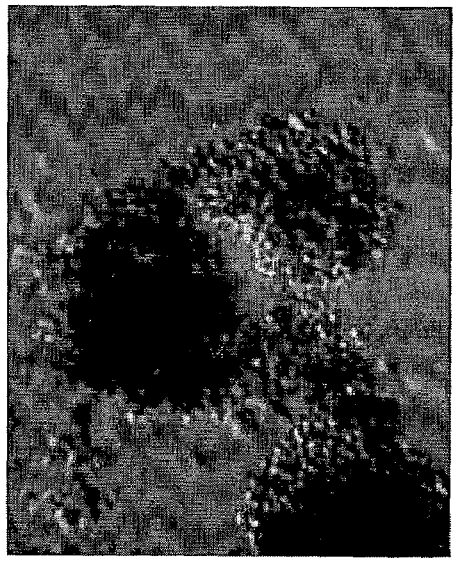
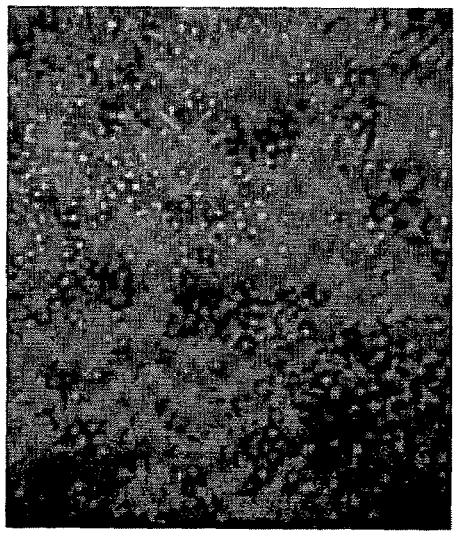
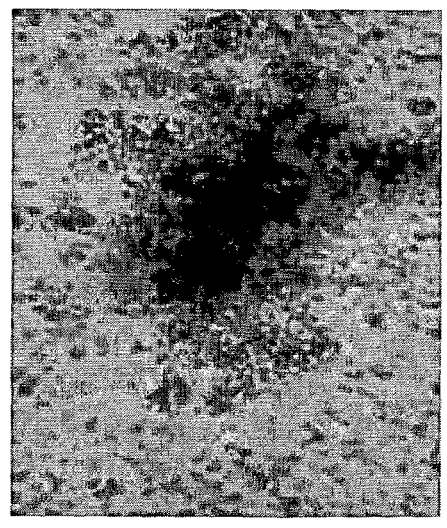
FIGURE 16A

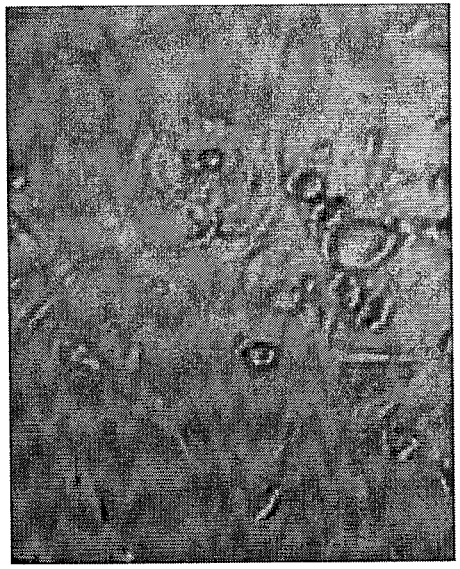
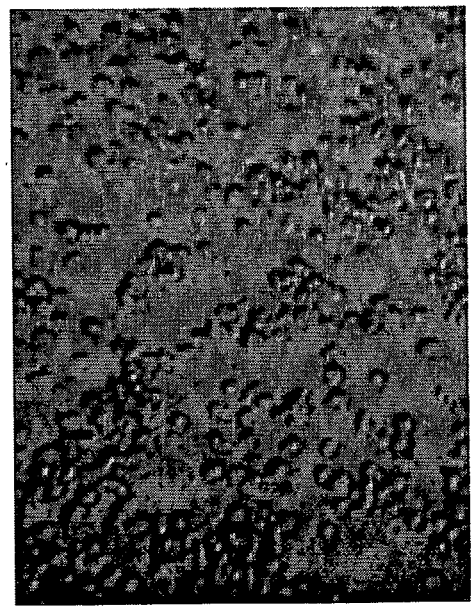
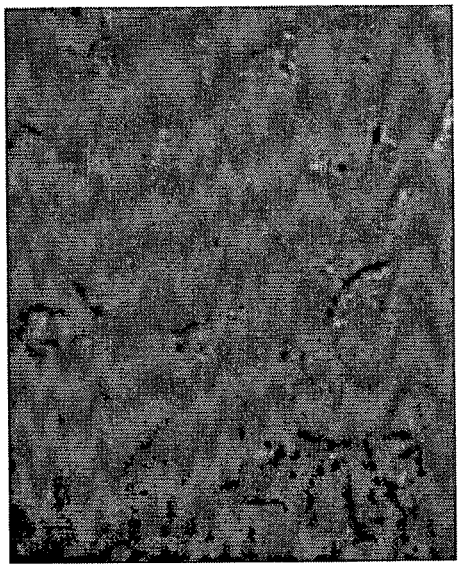
FIGURE 16B

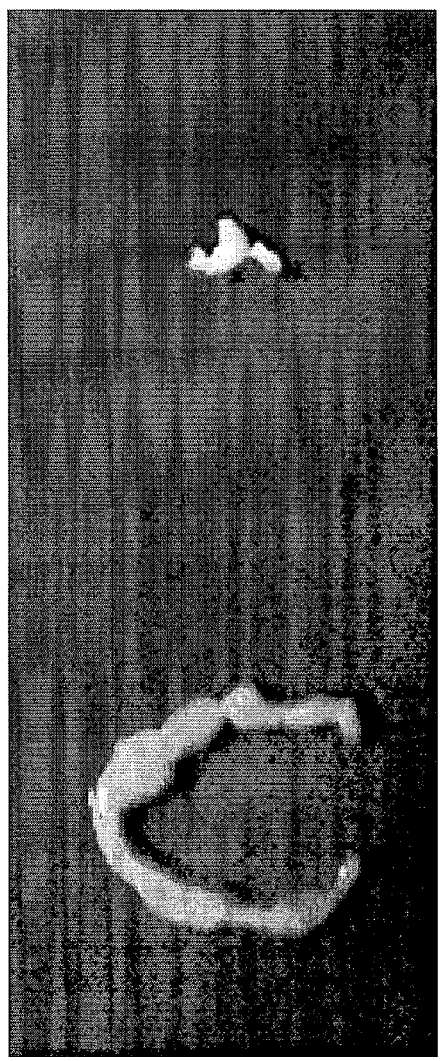
FIGURE 17A

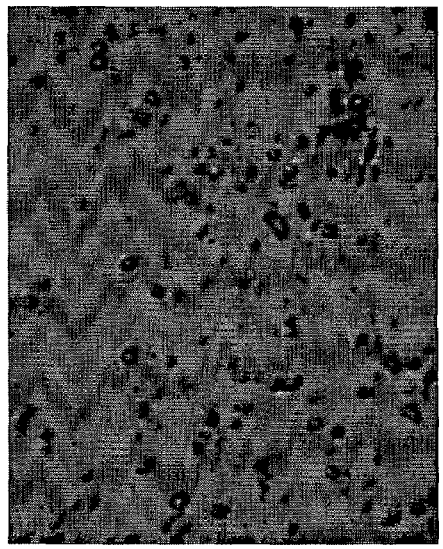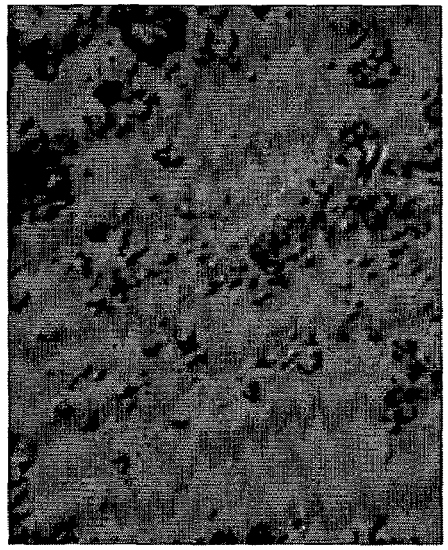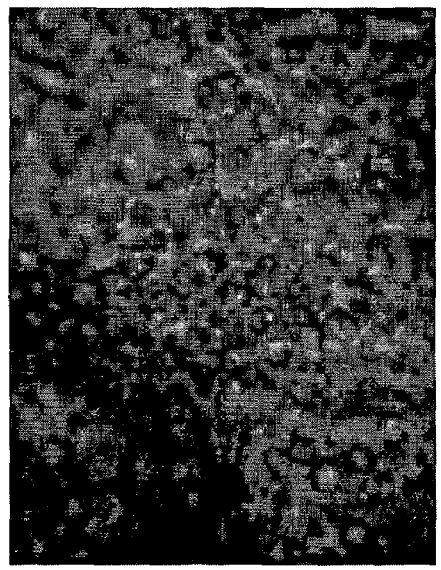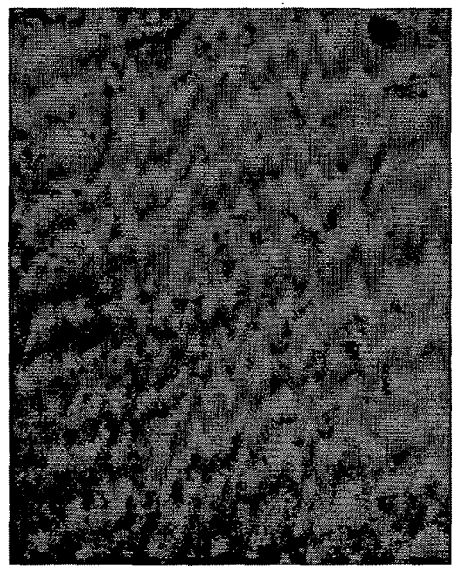
FIGURE 18

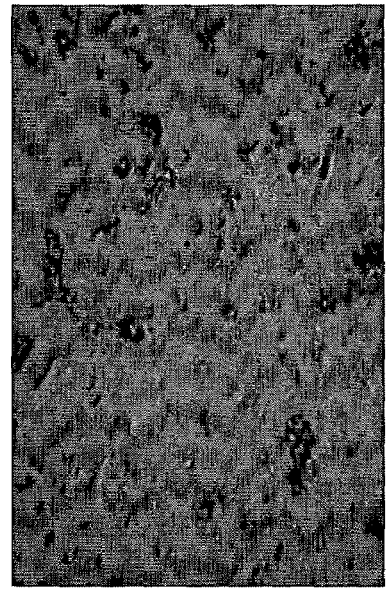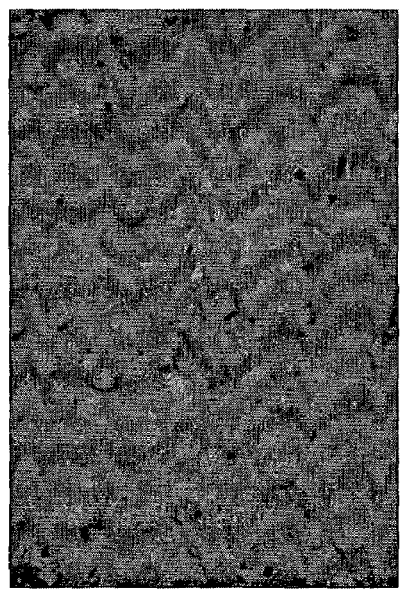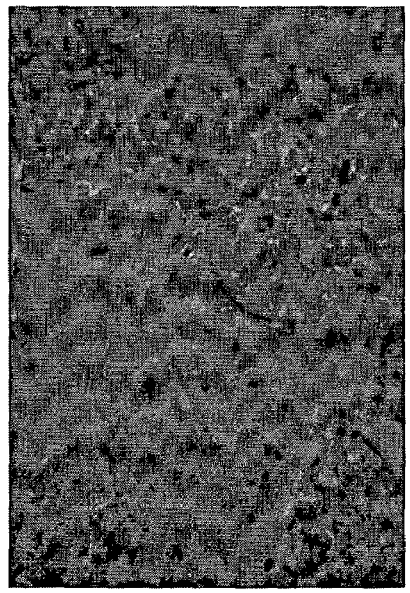
FIGURE 20

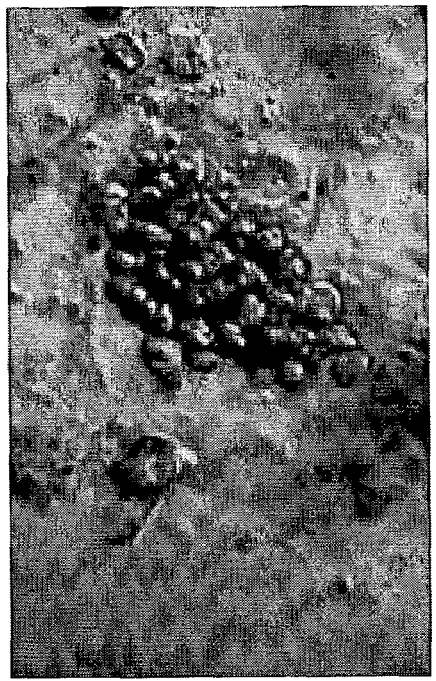
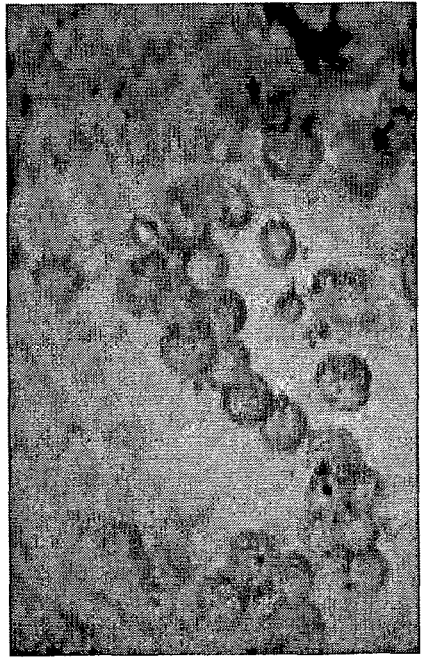
FIGURE 21A

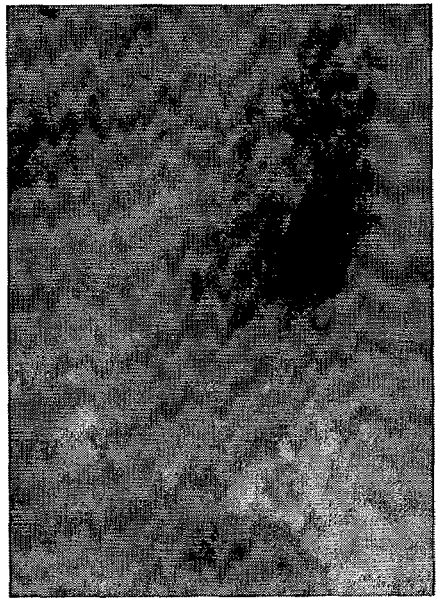
FIGURE 22

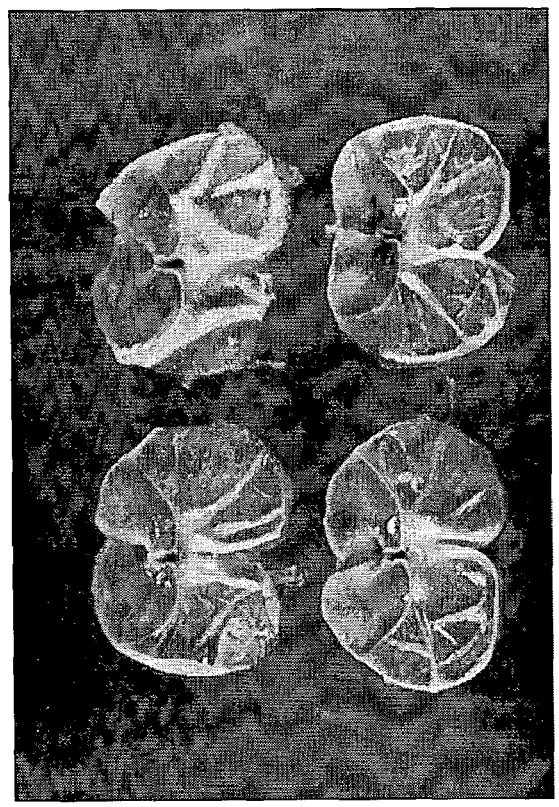
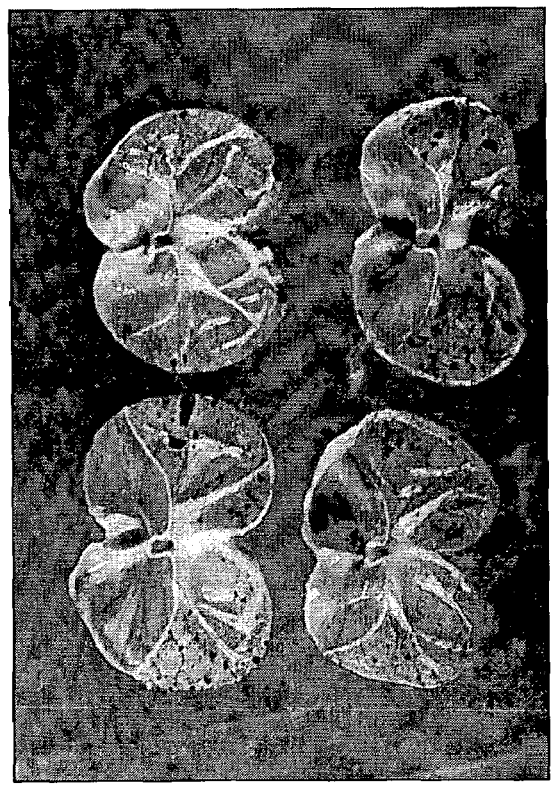
FIGURE 25

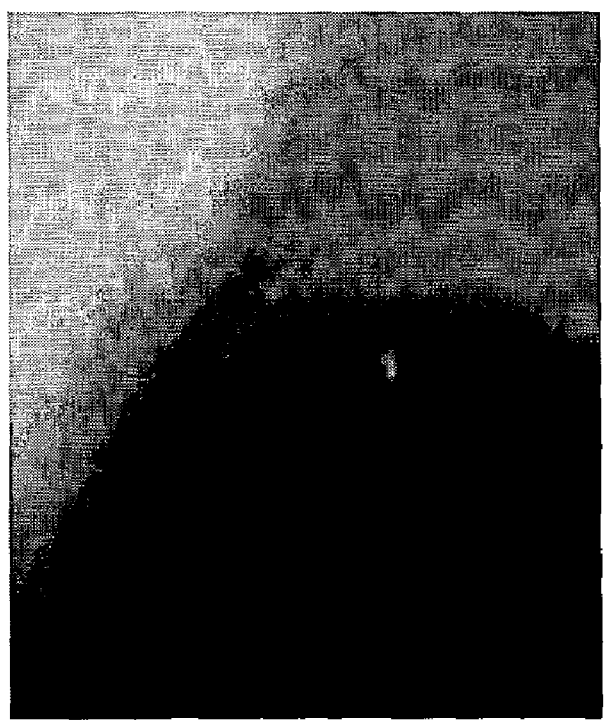
FIGURE 26

COMPOSITION AND METHOD FOR CULTURING POTENTIALLY REGENERATIVE CELLS AND FUNCTIONAL TISSUE-ORGANS IN VITRO

BACKGROUND OF THE INVENTION

Cross Reference to Related Application

This application claims priority to Chinese Patent Application entitled "Potentially Regenerative Cells", filed: Sep. 27, 2002, Chinese Patent Application Serial No: 02143546.4. This application is herein incorporated by reference in its entirety.

1. Field of the Invention

The present invention relates to compositions and methods for culturing cells, tissues, and organs in vitro, and more particularly to compositions and methods for controlled growth and differentiation of cells to generate functional tissues and/or organs in vitro, which can be used as in vitro model systems for nutraceutical and pharmaceutical studies and for tissue/organ repair and regeneration in vivo.

2. Description of the Related Art

Since the discovery of genetic materials in the middle of the 19th century, scientists have focused on the biochemistry of the genetic materials within a cell, which ultimately led to systematic studies of molecular biology of the cell. In the 20th century, after several decades of fanatic research on genes, rationality started to return in this area. Until the end of the 20th century—in the year of 1998 did scientists shift their attention to cell biology and resume the research on the embryonic development of the human body. Such a developmental process has been described by using the term "stem cells". It is also widely envisioned that embryonic stem cells can be cultured in vitro to generate various body organs such as hearts, kidneys and livers which can then be transplanted autologously back to the body for therapeutic purposes. It is further imagined embryonic stem cells can also be used as cell therapy by injecting the cells into the diseased site and causing the stem cells to repair and regenerate in situ, hopefully curing the disease eventually. These hopes still remain as fantasies because based on the state of the art it is yet to be seen that fundamental breakthroughs are made to overcome the frustrations encountered in identifying and culturing stem cells in vitro.

Generally, the current techniques in cell culture include isolating cells from the body, putting the cells in a sterile, nutritious environment mimicking that in vivo and at appropriate temperatures and pH levels, and letting the cells to grow while trying to maintain their structure and function. The subject of a cell culture includes single cells and cell clusters.

In the study of medical genetics, the most popular cell lines are peripheral blood lymphocytes (PBL), skin cells, fibroblasts and other cell lines that are able to sustain the growth for a long time in vitro. The advantages of PBL culture are: short operation time, simple techniques, materials repeated harvestable, etc. These cell line are utilized extensively for chromosome analysis in the clinic. The cells cultured in vitro can be transformed into immortalized cell lines automatically or in response to external stimuli. Or the immortalized cell lines can be established directly, which can divide and proliferate forever. The characteristics of the cell lines are 1) aneuploid, and 2) the karyotypes of different cells are not completely uniform. These characteristics are not as obvious for cell lines established from a cell colony.

It is required that the conditions of cell culture in vitro mimic the environment of cell growth in vivo. Therefore, non-toxic and sterile condition is most important of all. Compared to the cells in vivo, the cells lost the ability to defend against microbials and poisons when cells are cultured in vitro. They will die once they are contaminated or when self-metabolites are accumulated to a certain level. So the essential condition of cell culture in vitro is to maintain the sterile environment and discharge the metabolites.

The temperature is another key factor for tissue culture. The suitable temperature for human cells is 36.5° C.±0.5° C., and the normal metabolism of cells will be affected and the cells may die if the temperature is not within this range. The cultured cells can withstand hypothermia better than hyperthemia: when the temperature is less than 39° C., the cell metabolism and the temperature have a direct ratio; human cell will have certain level lesion when it's 39–40° C. for 1 hour, but it's repairable; when it's 40–41° C., the lesion will widespread to almost all cells, only a small half of cells can be repaired; when it's 41–42° C., the lesion is very serious, most of cell will die, but still it's possible for some cells to be repaired; when the cells is under 43° C. for 1 hour, all the cells will die.

Concentrations of gases, mainly oxygen and carbon dioxide, are also one of the essential conditions for cell culture. Oxygen is in involved in the tricarboxylic acid cycle, which produces the energy of cell proliferation and all kinds of components for cell growth. When the cell cultured in vitro in an ambient environment, they are incubated under the atmosphere of 95% air and 5% $CO_2$.

$CO_2$ is not only the metabolite of cell, but also the required component of cell growth and proliferation. The main function of $CO_2$ is maintaining the pH of the media. The suitable pH for most cells is 7.2–7.4, and cells will be adversely affected at a pH beyond this range. Since the cells can withstand acid better alkali, they tend to grow better in a slightly acidic environment. Studies have showed that the appropriate pH for primary amniotic cells is 6.8.

The most popular method for pH regulation of the media is to add $NaHCO_3$ into media, because $NaHCO_3$ can provide $CO_2$. But since $CO_2$ is easy to evaporate, so this method is suitable for tissue culture in a closed environment. Since HEPES is not toxic to cells and can be used for cell culture, it is advantageously used to maintain the pH of the media under an ambient condition.

The media for cell culture is also very important for cell culture. It not only provides the essential materials for cell growth and proliferation, but also forms the environment of cell living. There are a lot of kinds of media, they can be divided into semisolid medium and liquid medium based the form of the materials used. If categorized according to the sources of supply, they can be divided as synthetic medium and natural medium.

Synthetic medium is produced strictly based on the types and quantity of substances required by cell growth. It includes carbohydrates, amino acids, lipids, inorganic salts, vitamins, minerals, and cell growth factors. When synthetic media are used alone, the cells are alive, but they can't proliferate well.

The most common natural medium is serum, especially bovine serum. There are a lot of cell growth factors, adhesion-promoting factors and other live materials in serum. Used together with synthetic media, the natural medium allows the cells to grow and proliferate actively. The common concentration is 5–20% serum in the synthetic media.

The cells cultured in vitro can be divided into 2 large groups based on their growth characteristics. Group 1 are attached cells: they adhere to the substrate of the container when they are cultured in vitro, such as amniocytes. Group 2 are suspended cells: they can suspend in the medium in vitro. The most common attached cells are: fibroblasts, epithelial cells and wandering cells.

All the cells, which have similar shape with fibroblast, can be called fibroblast-like cells. They got their name because they have a shape similar to that of fibroblasts in vivo. They have a fusiform shape or adopt an irregular triangle form on the surface of dishes or flasks; there is a ovum nuclear in the central of cell, cytoplasm expended outside for 2–3 cm. The cells originated from mesoderm often grow like this except for true fibroblasts.

Epithelial cell-like cells are thin and flat with irregular multi-angles on the surface of dishes (or other substrates). When cultured in vitro, the nuclear is round and in the center of the cell, all the cells are connected to each other tightly to form a single layer. Cells originated from ectoderm or endoderm such as skin, skin derivative or epithelial cells of the digestive tract all belong to this group.

Wandering cells scatter in the media and normally don't join each other to form clusters. Cytoplasm often stretches out as pseudopodium or apophysis. The cells moved actively and there are a lot of amoeboid movements, very fast and randomly. These cells are not very stable and sometimes are difficult to be distinguished with other cells. Under certain conditions, when the density of cells increases, the cells are connected to each other to form multi-angle shape or fibroblast-like shape cells such as early stage amniotic cells.

The shapes of cultured cells are different depending on the shape of the substrate. The most common one is the cell attaching to the flat surface. Under microscope, living cells are clear and smooth; the structure is not so obvious. There are always 1–2 nuclei when the cell is growing normally. When the cell is malfunctional, the profile of cell is manifested more saliently against the background. Sometimes there are granules or bubbles in cytoplasm, which indicates dysfunction of the cell metabolism.

When PBL are cultured in vitro using the techniques currently available, there are no splitting cells in peripheral blood under the normal condition, which only occurs when it's abnormal. PHA is a stimulator of mitosis of human lymphocytes. Under the promotion of PHA, lymphocytes change into lymphocytoblasts from $G_0$ phase, and then begin to undergo mitosis. By exploiting this character of PHA, abundant actively mitotic cells can be obtained by culturing lymphocytes in a medium containing PHA.

In addition, when preparing chromosomes from tissue culture cells, the most common ones in genetic analysis are the cell lines cultured in vitro, most of them being malignant tumor cell lines. These cell lines are attached cell lines, only a small part of them are suspended cell lines. They have the following advantages: readily available sources, high rate of cell division and the high resolution of chromosome specimen. The key to the preparation of tissue cell chromosomes is to understand and control the growth development of cell culture in vitro. Only cells in log growth period can have high mitotic rate. So the timing and dosing of colchicine for the cell is critical for proper preparation of cell chromosome specimen.

Epidermal stem cells have been cultured in vitro in order to generate keratinocytes for reconstructing autologous or allogenic epidermal sheets that can be used in skin transplantation in wound healing. To provide a large amount of keratinocytes, great efforts have been made to cultivate human epidermal stem cells in culture. In preparing epidermal sheets for transplant basal keratinocytes are cultivated in culture to produce large numbers of progeny. Maintaining these stem cells in culture conditions can be challenging. The quality of the keratinocyte culture system must be carefully monitored by directly demonstrating the presence of holoclones in culture, periodical clonal analysis of a reference strain of keratinocyte both in terms of clonogenic and growth potential, and monitoring the percentage of aborted colonies. Inappropriate culture conditions can irreversibly accelerate the clonal conversion and can rapidly cause the disappearance of stem cells, rendering the cultured autograft or allograft transplantation useless.

Besides keratinocyte stem cells, other types of stem cells are cultivated in cell culture in an attempt to provide sufficient amount of cells for tissue repair or other therapeutic use. Embryonic stem (ES) cells can be cultured under proper conditions. Thomson et al. demonstrated that cells from the inner cell mass (ICM) of mammalian blastocysts can be maintained in tissue culture under conditions where they can be propagated indefinitely as pluripotent embryonic stem cells. Thomson et al. (1998) Science 282:1145–1147. Primate blastocysts were isolated from the ICM from the blastocysts and plated on a fibroblast layer wherein ICM-derived cell masses are formed. The ICM-derived cell mass were removed and dissociated into dissociated cells which were replated on embryonic feeder cells. The colonies with compact morphology containing cells with a high nucleus/cytoplasm ratio, and prominent nucleoli were selected and the cells of the selected colonies were then cultured. In this way, a primate embryonic stem cell line was established. It was observed that after undifferentiated proliferation in vitro for 4 to 5 months, these cells still maintained the developmental potential to form trophoblast and derivatives of all three embryonic germ layers, including gut epithelium (endoderm); cartilage, bone, smooth muscle, and striated muscle (mesoderm); and neural epithelium, embryonic ganglia, and stratified squamous epithelium (ectoderm). Thus, it is envisioned that these ES cells can be cultured and regulated under suitable conditions to coax the pluripotent cell to differentiate into cells of a particular tissue type and/or to form various organs in vitro. These cells and organs, wishfully, could be used as transplants to cure various diseases and replace dysfunctional body parts.

Although desirable, an in vitro embryonic development process is highly unpredictable. The conditions under which ES cells differentiate into a specific type of cell or organ are elusive. It has been found that to maintain cultured ES cells in their relatively undifferentiated, pluripotent state, they must both express the intrinsic transcription factor Oct4, and constitutively receive the extrinsic signal from the cytokine leukemia inhibitor (LIF). Nichols et al. (1998) Cell 95:379–391. Upon withdrawal of LIF, cultured ES cells spontaneously aggregate into a mass of cells of various tissue types. Although the programs of gene expression in these cells somewhat resemble the differentiation pathways typical of developing animals, the triggering of these programs is chaotic.

For successful organ regeneration in the clinic using stem cells cultured in vitro, a major obstacle lies in its way. Stem cells cultured in vitro must be directed to differentiate into site-specific phenotypes once they are transplanted into the lesion site. Complete deciphering of the signal needed for this process is required to guide the design of the in vitro tissue culturing conditions. Experimental data obtained by others in the art show that although multipotent human mesenchymal, mouse neural stem cells, and mouse embryonic stem cells can be grown in vitro through the addition of leukemia inhibitory factor (LIF) to the culture medium, mouse ESCs differentiate randomly in vitro and in vivo. Progress in the art has made it possible to induce differentiation of mouse ESCs into multipotent glial cell precursors in vitro and to transplant them into the brain of myelin-deficient fetal rats. However, question remains unanswered as to whether these multipotent stem cells harvested from specific tissues or differentiated from ESCs in vitro will make site-specific tissue when transplanted to injured adult tissues.

Up to date enormous amounts of money and efforts have been made in attempts to repair damaged tissue and dysfunctional organs through cultivation of stem cells in vitro. However, as discussed above, the culturing process is tedious and requires addition of a delicately balanced "cocktail" composed of costly protein growth factors to maintain proliferation of the stem cells, and the directional differentiation of the stem cells is often difficult to control, depending on multiple factors, and irreproducible.

In summary, the current cell culture techniques developed by others so far have been shown to be able to maintain the growth and proliferation of cells obtained from the body. It is rarely seen that normal, somatic cells from an adult body can be cultured in vitro to generate physiologically functional tissue or tissue-organ.

SUMMARY OF THE INVENTION

The present invention provides innovative compositions and methods for culturing in vitro potentially regenerative cells (PRCs) from which functional tissues and organs are regenerated. The invention stems from the inventor's novel theory that 1) PRCs are "reserved" copies of cells produced during the development of the body; 2) when the body is fully developed, these PRCs exist as regular tissue cells in the adult body but maintain the ability or potential to proliferate and differentiate in response to the cues of renewal, repair and regeneration of tissues and organs in situ; and 3) under suitable regenerative conditions and environment, the PRCs are activated to become regenerative stem cells which proliferate and directionally differentiate to produce tissue cells needed for tissue/organ renewal, repair and regeneration in vivo and in situ.

Guided by this fundamental theory, a series of in vitro experiments were designed and conducted to show that PRCs indeed exist in a wide variety of tissues and organs in the body, and PRCs isolated from different sites of the body can be activated and converted into regenerative stem cells in a tissue culture medium comprising the inventive composition and produce in vitro tissues and/or organs with substantially the same physiological structure and function as the corresponding ones existing in vivo and in situ. Such tissues and/or organs are herein referred to as "tissue-organs".

In one aspect of the invention, a cell growth regulator is provided, comprising: a sterol compound that is dissolved in a fatty acid-containing oil at a concentration at least 0.1% by weight based on the weight of the oil. The sterol compound preferably forms ester with the fatty acid in the oil under suitable conditions such as at high temperatures (e.g., >100° C.).

In another aspect of the invention, a tissue culture medium is provided, comprising: at least 50% of water and a sterol compound that is dissolved in a fatty acid-containing oil at a concentration at least 0.1% by weight based on the weight of the oil and added to the water. The sterol compound preferably forms ester with the fatty acid in the oil under suitable conditions such as at high temperatures (e.g., >100° C.).

The concentration of the oil in the tissue culture medium preferably ranges from about 1% to 50% by weight, more preferably about 5% to 30% by weight, and most preferably about 10% to 20% by weight.

The concentration of the sterol compound in the oil preferably ranges from about 0.5% to 40% by weight, more preferably about 1% to 20% by weight, and most preferably about 2% to 6% by weight.

The fatty acid-containing oil is preferably vegetable oil, more preferably vegetable oil selected from the group consisting of corn oil, peanut oil, cottonseed oil, rice bran oil, safflower oil, tea tree oil, pine nut oil, macadamia nut oil, camellia seed oil, rose hip oil, sesame oil, olive oil, soybean oil and combinations thereof, and most preferably sesame oil.

The fatty-acid is preferably selected from the group consisting of palmitic acid, linoleic acid, oleic acid, trans-oleic acid, stearic acid, arachidic acid, and tetracosanoic acid.

According to this embodiment, the culture medium may further comprise wax that is dissolved in the fatty acid-containing oil and added to the water. The concentration of the wax preferably ranges from about 1% to 20% by weight, more preferably from about 2% to 10% by weight, and most preferably from about 3% to 6% by weight based on the weight of the oil.

The wax is preferably edible wax, more preferably edible wax selected from the group consisting of beeswax, castorwax, glycowax, and carnaubawax, and most preferably beeswax.

In yet another aspect of the invention, a method for culturing potentially regenerative cells in vitro is provided. The method comprises: isolating tissue cells or a tissue from a predetermined site of the body of a mammal; and culturing the isolated tissue cells or tissue in a tissue culture medium under suitable conditions such that potentially regenerative cells contained in the isolated tissue cells or cells migrated from the isolated tissue are activated to continuously proliferate and differentiate to form a tissue-organ which shares substantially the same physiological structure and at least one physiological function with that of the corresponding tissue in situ and in vivo.

The mammal may be a rodent, a primate or a human, preferably a primate, more preferably a human, and most preferably an adult human. The mammal from which the tissue cells or tissues are isolated is preferably alive. Optionally, the mammal may be dead but the tissue cells or tissue are still viable.

The isolated tissue cells or tissues may be isolated from any site of the body of the mammal, for example, the brain, heart, liver, lung, intestine, stomach, kidney, bone marrow, and skin. The isolated tissue cells are not embryonic stem cells, and the isolated tissue is not from the blastocyst of the mammal.

Optionally, when a tissue is isolated from the body of the mammal, the tissue is processed in vitro to produce cells which are then isolated and cultured in the culture medium of the present invention to produce the tissue-organ.

The culture medium may comprise at least 50% of water and a sterol compound that is dissolved in a fatty acid-containing oil at a concentration at least 0.1% by weight based on the weight of the oil and added to the water. The sterol compound preferably forms ester with the fatty acid in the oil under suitable conditions such as at high temperatures (e.g., >100° C.).

The potentially regenerative cells contained in the isolated tissue cells or tissue may be activated in the culture medium to continuously proliferate and differentiate for at least 5 days, preferably for at least 10 days, more preferably for at least 30 days, and most preferably for at least 50 days.

The tissue-organ formed in the culture shares at least one physiological function with that of the tissue in situ and in vivo, for example, the ability to produce molecules with biological activities such as enzymatic activity, signaling and regulatory functions, and the ability to cause muscle contraction in response to electric current.

According to any of the above embodiments, the sterol compound may be an animal sterol or a plant sterol (also called phytosterol). Examples of animal sterol include cholesterol and all natural or synthesized, isomeric forms and derivatives thereof. Preferably, the sterol compound is selected from the group consisting of stigmasterol, campesterol, β-sitosterol, chalinosterol, clionasterol, brassicasterol, α-spinasterol, daucosterol, avenasterol, cycloartenol, desmosterol, poriferasterol, and all natural or synthesized, isomeric forms and derivatives thereof. More preferably, the sterol compound is a combination of stigmasterol, β-sitosterol, and campesterol, collectively referred to herein as "sitosterol".

Optionally, the sterol compound is a combination of stigmasterol and β-sitosterol.

Also optionally, the sterol compound is a combination of brassicasterol and β-sitosterol.

Also optionally, the sterol compound is a combination of brassicasterol, stigmasterol and β-sitosterol.

Also optionally, the sterol compound is a combination of campesterol, stigmasterol and β-sitosterol.

It is to be understood that modifications to the sterol compound i.e. to include side chains also fall within the purview of this invention. It is also to be understood that this invention is not limited to any particular combination of sterols forming a composition.

According to any of the above embodiments, the culture medium may further comprise baicalin dissolved in the oil, preferably at a concentration ranging from about 0.001 to 2% by weight, more preferably about 0.02 to 1% by weight, and most preferably about 0.02% to 0.5% by weight based on the total weight of the oil.

According to any of the above embodiments, the oil in the culture medium is an oil-extract of huanglian wherein the amount of huangqin is 2–60% by weight based on the total weight of the oil.

Also according to any of the above embodiments, the culture medium may further comprise obaculactone dissolved in the oil, preferably at a concentration ranging from about 0.001 to 2% by weight, more preferably about 0.02 to 1% by weight, and most preferably about 0.02% to 0.5% by weight based on the total weight of the oil.

According to any of the above embodiments, the oil in the culture medium is an oil-extract of huangbai wherein the amount of huangqin is 2–60% by weight based on the total weight of the oil.

Optionally, the culture medium may further comprise obabenine, preferably at a concentration ranging from about 0.001% to 2% by weight, more preferably about 0.002% to 0.5% by weight, and most preferably about 0.003% to 0.1% by weight based on the total weight of the oil.

According to any of the above embodiments, the oil in the culture medium is an oil-extract of huanglian wherein the amount of huangqin is 2–60% by weight based on the total weight of the oil.

Also optionally, the culture medium may further comprise berberine, preferably at a concentration ranging from about 0.001% to 2% by weight, more preferably about 0.002% to 0.5% by weight, and most preferably about 0.003% to 0.1% by weight based on the total weight of the oil.

Also optionally, the culture medium may further comprise narcotoline, preferably at a concentration ranging from about 0.001% to 2% by weight, more preferably about 0.002% to 0.5% by weight, and most preferably about 0.003% to 0.1% by weight based on the total weight of the oil.

In a particular embodiment, the oil in the culture medium is an oil-extract of huangqin containing baicalin at a concentration ranging from about 0.001 to 2% by weight based on the total weight of the oil, wherein the sterol compound is a phytosterol and the oil is sesame oil.

Also optionally, the oil in the culture medium is an oil-extract of heshouwu wherein the amount of heshouwu is 2–60% by weight based on the total weight of the oil.

Also optionally, the culture medium may further comprise various amino acids, preferably all 20 natural amino acids (e.g., alanine, asparagines, aspartic acid, cysteine, glutamic acid, glutamine, glycine, phenylalanine, histidine, isoleucine, lysine, leucine, methionine, proline, arginine, serine, threonine, valine, tryptophan, and tyrosine), for providing nutrition support to cell growth. The amino acids may be chemically synthesized or obtained from natural sources. For example, a full spectrum of natural amino acids may be obtained by extracting earthworms, a rich source of protein/amino acids, in oil or alcohol.

In a particular embodiment, the oil in the culture medium is an oil-extract of earthworm wherein the amount of earthworm is 2–60% by weight based on the total weight of the oil.

In yet another aspect of the invention, isolated potentially regenerative cells from a predetermined site of the body of a live mammal are provided. The isolated potentially regenerative cells, when cultured in a culture medium under suitable conditions, are capable of being activated to continuously proliferate and differentiate to form a tissue-organ which shares substantially the same physiological structure and at least one physiological function with that of the corresponding tissue in situ and in vivo.

The potentially regenerative cells may be isolated from any site of the body of the mammal such as an adult body of a human, for example, the brain, heart, liver, lung, intestine, stomach, kidney, bone marrow, and skin. The isolated potentially regenerative cells are not embryonic stem cells, and are not from the blastocyst of the mammal.

The culture medium may comprise at least 50% of water and a sterol compound that is dissolved in a fatty acid-containing oil at a concentration at least 0.1% by weight based on the weight of the oil and added to the water. The sterol compound preferably forms ester with the fatty acid in the oil under suitable conditions such as at high temperatures (e.g., >100° C.).

The isolated potentially regenerative cells, when cultured in the culture medium, may be able to continuously proliferate and differentiate for at least 5 days, preferably for at least 10 days, more preferably for at least 30 days, and most preferably for at least 50 days.

The compositions and methods of the present invention can be utilized to generate in vitro a large amount of regenerative cells, tissues and/or organs with normal physiological structure and function. These biological materials can serve as extremely valuable models for basic scientific investigation in every aspect of life sciences, and be utilized in many practical applications such as nutraceutical discovery, drug screening, pharmacokinetic studies, medical devices and tissue/organ transplantation.

BRIEF DESCRIPTION OF THE FIGURES

FIG. 6 shows explants of mouse intestine culture in the presence (left panel) and absence (right panel) of the inventive composition.

FIG. 7 shows explants of mouse intestine cultured for 60 days in the presence (left panel) and absence (right panel) of the inventive composition.

FIG. 9 shows that clones of intestinal cells (left panel) adhere to each other to form intestinal mucosal tissue (right panel).

FIG. 10 shows the end of an intestinal villus formed in the culture (left panel, its magnified image shown in the right panel).

FIG. 14 compares the basic structure of the cloned intestinal villus according the present invention (right panel) with that obtained from a tissue section of the intestine of a mouse fetus (left panel).

FIG. 15 compares the structure of the cloned intestinal villus according the present invention (right panel, its magnified image shown in the upper left panel) with that obtained from a tissue section of the intestine of a mouse fetus (lower left panel).

FIG. 16A shows proliferation and differentiation of progenitor cells (upper left panel) in mouse bone marrow into small colonies (lower left panel) which evolved into bone marrow tissue (lower right panel) gradually. Control cells are shown in the upper right panel.

FIG. 16A shows proliferation and differentiation of progenitor cells (upper left panel) in mouse bone marrow into small colonies (lower left panel) which evolved into bone marrow tissue gradually (moving from the lower to the upper right panel).

FIG. 16B shows progenitor cells (upper left panel) in mouse bone marrow cultured in the absence of the inventive composition only yielded more and more fibroblasts (moving from the lower left panel to the lower right panel and then to the upper right panel).

FIG. 17A shows regenerated nerve tissues in the presence (left side of the upper and lower panels) the inventive composition and degenerated nerve tissue in the absence of the inventive composition (right side of the upper and lower panels).

FIG. 18 shows cloned pancreatic tissue after culture in the presence of the inventive composition for 65 (upper left panel) and 92 days (lower left panel), and necrosis of pancreatic cells in the absence of the inventive composition for 65 (upper right panel) and 92 days (lower right panel).

FIG. 20 shows the cloning of renal structure units (lower left panel and upper right panel) from renal cortical cells (upper left panel). Renal cortical cells died in the control group (lower right panel).

FIG. 21A shows that single cells (upper left panel) isolated from human hair follicles proliferated and differentiated in vitro to form colonies (lower left panel), the basic structure of a hair follicle (lower right panel) and a completely cloned hair follicle.

FIG. 22 shows that mouse cardiomuscular cells (upper left panel) were cultured in vitro to gradually form cardiomuscular tissue (moving from the lower left panel to the lower right panel and then to the upper right panel).

FIG. 25 shows treatment of acute gastric ulcer of mice with an embodiment of the inventive composition (right panel: test group; left panel: control group).

FIG. 26 shows treatment of gastric ulcer of a patient mice with an embodiment of the inventive composition (left panel: before treatment; right panel: after treatment).

DETAILED DESCRIPTION OF THE INVENTION

Figure 1:
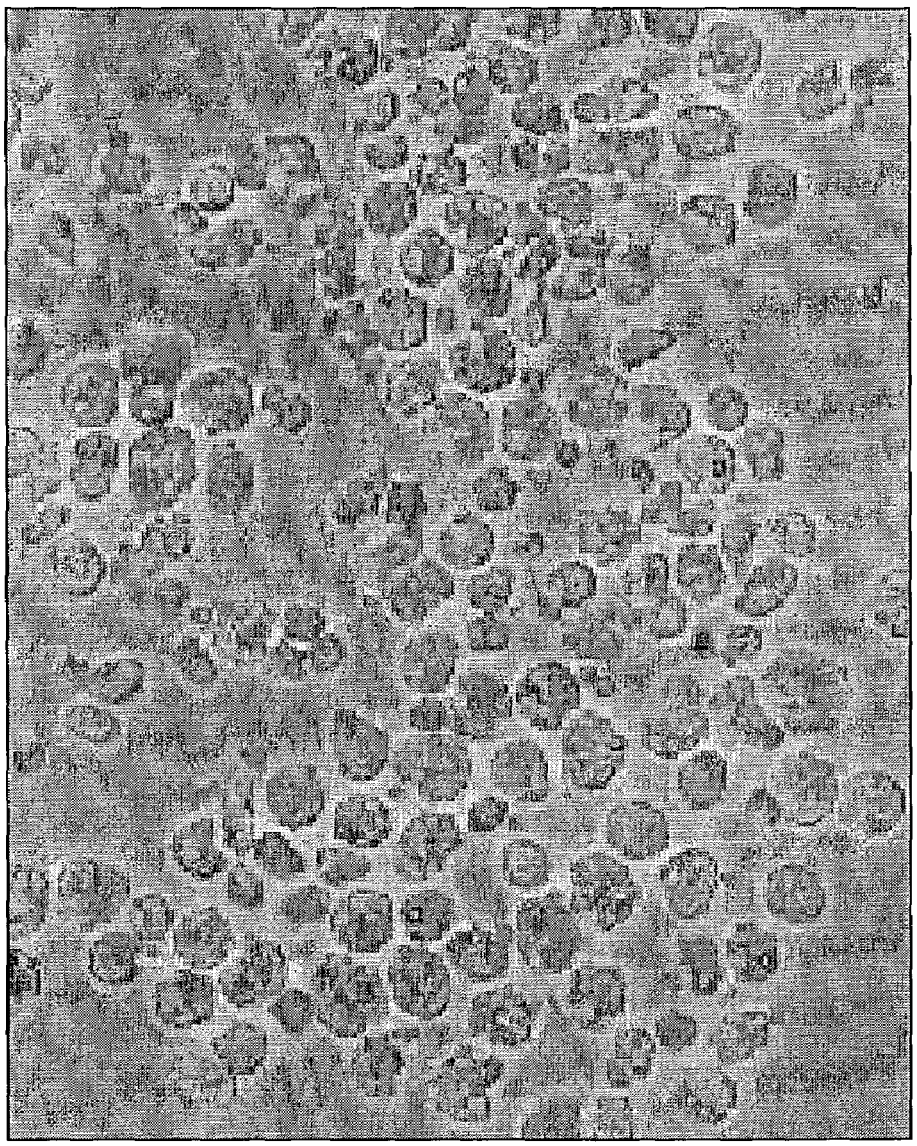
FIG. 1 shows human intestinal cells cultured for 55 days in vitro in the present of the inventive composition.

The present invention provides innovative compositions and methods for culturing potentially regenerative cells (PRCs) from which functional tissues and organs are regenerated in vitro. Also provided are isolated cells that possess regenerative potential and are capable of being cultured to generate in vitro a functional tissue or organ having substantially the same physiological structure and function as the corresponding tissue or organ residing in vivo and in situ. The composition and methods of the present invention can be utilized to generate in vitro a large amount of PRCs, tissues and/or organs with normal physiological structure and function. These biological materials can serve as extremely valuable models for basic scientific investigation in every aspect of life sciences, and be utilized in many practical applications such as nutraceutical discovery, drug screening, pharmacokinetic studies, medical devices and tissue/organ transplantation.

The invention stems from the inventor's novel theory that 1) PRCs are "reserved" copies of cells produced during the development of the body; 2) when the body is fully developed, these PRCs exist as regular tissue cells in the adult body but maintain the ability or potential to proliferate and differentiate in response to the cues of renewal, repair and regeneration of tissues and organs in situ; and 3) under suitable regenerative conditions and environment, the PRCs are activated to become regenerative stem cells which proliferate and directionally differentiate to produce tissue cells needed for tissue/organ renewal, repair and regeneration in vivo and in situ.

Guided by this fundamental theory, a series of in vitro experiments were designed and conducted to show that PRCs indeed exist in a wide variety of tissues and organs in the body, and PRCs isolated from different sites of the body can be activated and converted into regenerative stem cells in a tissue culture medium comprising the inventive composition and produce in vitro a tissue and/or organ with substantially the same physiological structure and function as the corresponding one existing in vivo and in situ.

During the in vitro experiments it was observed that when somatic tissue cells were isolated from an adult and cultured in vitro (as isolated cells or explants) in the inventive culture medium, there were some cells that appeared to share the same morphology as the rest of the cells but possessed an unusual potential to be activated to behave like regenerative stem cells. Initially, these cells remained dormant in the culture but was activated within a few days of culture to manifest the ability of a stem cell—to not only constantly proliferate but also directionally differentiate to generate a tissues and/or organ by following a lineage specific to the site of the body where they were originally isolated from. Tissue cells have such characteristics are termed "PRCs". While not wishing to be bound to the theory, the inventor believes that PRCs differ from classic stem cells in the several aspects.

Although the definition of stem cells still remains controversial and subject to changes in the techniques of identification in the field, a classic definition of a stem cell is that a stem cell should have the following properties: 1) It is not itself terminally differentiated, i.e., not at the end of a pathway of differentiation; 2) It can divide without limit or at least for the life time of the animal; and 3) When it divides, each daughter cell can either remain a stem cell, or embark on a course leading irreversibly to terminal differentiation. In Molecular Biology of the Cell, Alberts et al., eds, $3^{rd}$ ed. (1994), pp. 1155–1156, Garland Publishing Inc., New York and London. According to this definition, stem cells isolated from human tissue, such as the embryonic stem cells isolated from the inner cell mass of human blastocysts, hematopoietic stem cells from the blood, and epidermal stem cells from the basal layer of the skin are typical stem cells. Recently, adult stem cells (ASCs) have been discovered in the liver, pancreas, and central nervous system. See review by Fuchs and Segre (2000) Cell 100:143–155. The locations of ASCs have been searched extensively and speculated by others to be residing in specific "niches".

The inventor believes that PRCs exist in virtually every tissue and organ of the body and may not need specific "niches" to be tucked away. As shown in the Example section below, in all of the tissues isolated from mammals PRCs were identified and able to be activated, proliferate continuously and directionally differentiate to produce various tissue cells that eventually form a functional "tissue-organ" (See definition below) in vitro.

The inventor also believes that PRCs are duplicates of cells produced during the body's development from an embryo to a fully developed adult. PRCs tend to stay dormant in the body whereas typical stem cells are more dynamic in nature, i.e., undergo constantly renewal at different rates depending on where they reside, such as the constant renewal of epidermal stem cells from the basal layer of the skin. When there is a need for repair and regeneration, for example, a tissue/organ damage occurring in the body, PRCs can be mobilized to start the repair job if suitable regenerative conditions are provided. Once activated, PRCs appear to behave like typical stem cells: constantly proliferate and differentiate to produce large numbers of tissue cells. Under the environment provided by the inventive culture medium, these activated PRCs do not differentiate chaotically. Instead, the differentiation follows a lineage specific to the site of the body where the PRCs are originally isolated from. The activated PRCs that are going through this dynamic process are herein termed as "regenerative stem cells". It is noted that although PRCs can be precursors of regenerative stem cells, typical stem cells (adult or embryonic) participating the regeneration process also fall within the scope of the regenerative stem cells.

Figure 5:
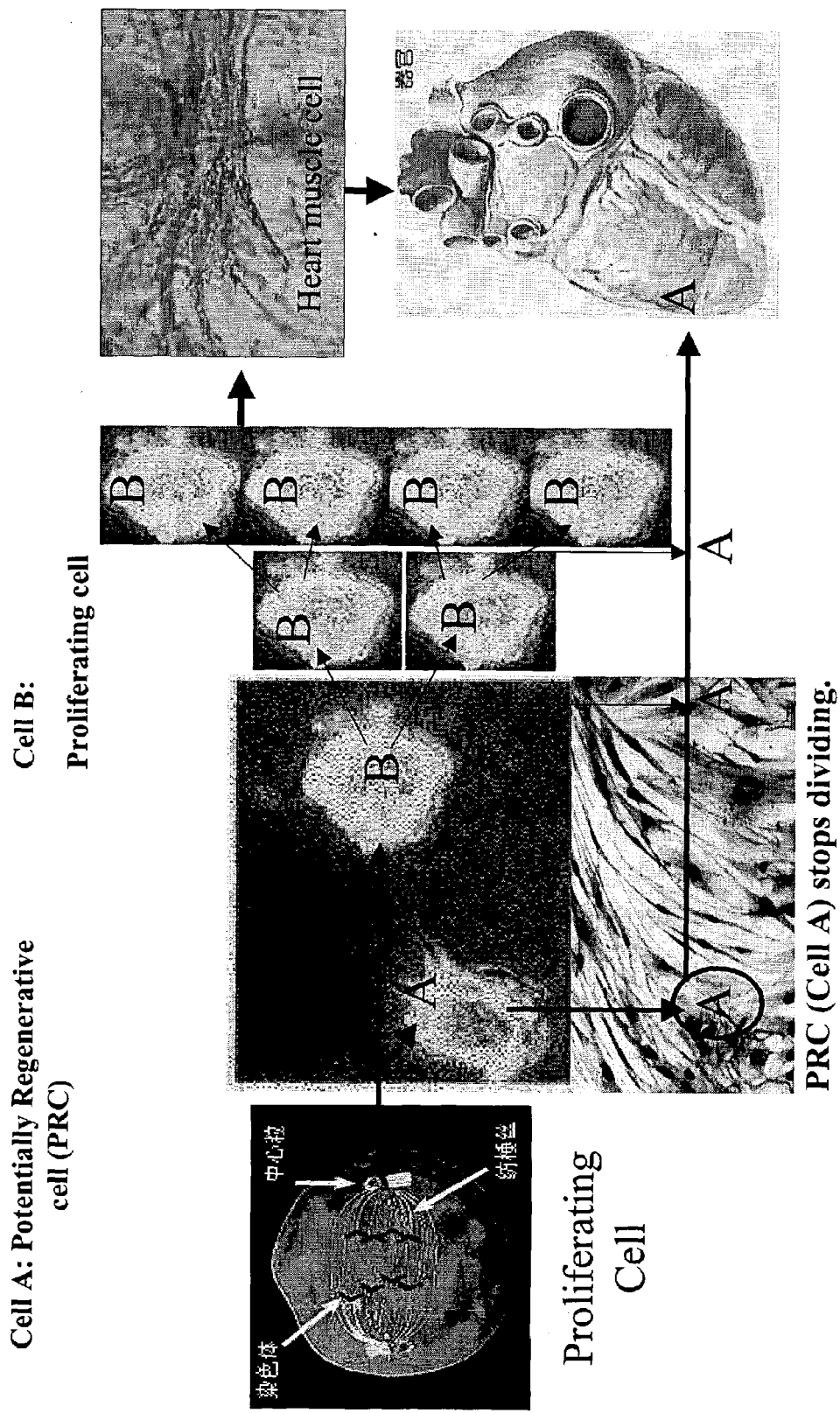
FIG. 5 illustrates a dynamic model of the proliferation and differentiation of potentially regenerative cells (PRCs) in vivo and in situ.

A dynamic model of PRCs is hypothesized and illustrated in FIG. 5. PRCs exist in every tissue or organ of the body (e.g., the heart) and can be originated from asymmetric division of a proliferating cell. One of the two daughter cells (cell B, e.g., a heart muscle cell, FIG. 5) is committed to further proliferation for the development of the organ while the other (cell A, FIG. 5) stops proliferation and remains dormant. Cell A may be undifferentiated, partially differentiated or permanently differentiated. However, when the body is injured or dysfunctional, in response to the cues of renewal, repair and regeneration of tissues and organs the dormant cells (cell A) in situ are activated. Under suitable regenerative conditions and environment, these cells (cell A) start to proliferate and directionally differentiate to produce tissue cells needed for tissue/organ renewal, repair and regeneration in vivo and in situ. These cells (cell A, FIG. 5) with the potential to proliferate and directionally differentiate for the body's repair and regeneration are the PRCs.

The inventor discovered that the PRCs, when isolated from any organ or tissue of the body and cultured under suitable regenerative conditions in vitro, can proliferate and directionally differentiate into a tissue-organ with substantially the same physiological structure and function as that in vivo and in situ. A tissue-organ is herein defined as a unit in any organ or tissue of the body that plays not only structural but also functional role(s) in maintaining the vitality of the body. The tissue-organ is a tissue or a composite of several tissues, which can be composed of a single or several types of cells. While not wishing to be bound by the theory, the inventor believes that there may be about 206 tissue-organs in a human body, which are classified according to the definition of "tissue-organ" provided herein.

For example, the intestinal villi is such a tissue-organ. It is known that intestinal villi are composed of epithelial cells, goblet cells, Paneth cells, and endocrinal cells. While these cells adhere to each other to form the distinct brush-like structure of intestinal villi, goblet cells in the villi function to secret mucus which is essential for protecting the intestine from the harmful effects of exogenous materials such as food and drinks, as well as for digesting these foreign materials in order to provide nutrients to the body.

Similarly, physiologically functional units in the body, such as hair follicles, pancreatic ducts, pancreatic islets, bone marrow, and ganglia, are examples of tissue-organs according to the present invention. As will be shown in detail in the EXAMPLE section below, PRCs isolated from various organ or tissue of the body could be cultured in vitro under suitable conditions to proliferate and directionally differentiate into a tissue-organ corresponding to the one from which the PRCs were originally isolated.

The discovery of the PRCs and their potential to develop into functional tissue-organs in vitro under suitable regenerative conditions has profound significance in both theory and practice.

The mainstream theory in the art is that once an organ of a fully developed adult body is injured or dysfunctional, it is almost impossible to rely on the body itself to completely heal. The popular remedial approach is to replace the failing organ and damaged tissue with organ transplantation and implantation of bionic device. The major drawbacks to organ transplantation are donor shortages and immunosuppressive side effects. The drawback to the approach of implantation of bionic device is the inability to manufacture artificial materials that duplicate the durability, strength, form, function, and biocompatibility of natural tissues.

The inventor believes that a fully developed adult body can regenerate itself through activation of PRCs residing in every organ or tissue of the body if suitable regenerative conditions are provided. This regeneration requires active intervention by delivering compounds or compositions to the damaged tissue or organ where they function to activate the PRCs and maintain the proliferation and directional differentiation of the PRCs in vivo and in situ. The compounds or compositions with such functions are herein defined as "vital substances". As a result, the newly generated cells and tissues from the body itself serve to repair the dysfunctional tissue or organ without going through transplantation.

According to the present invention, compositions and methods are provided for isolating and culturing PRCs in vitro. The cultured PRCs can develop into functional a tissue-organ with substantially the same physiological structure and function as the one from which the PRCs were originally isolated. The cultured PRCs and tissue-organ can serve as an in vitro model for studies of cell/tissue/organ development, validation of clinical results, and screening for therapeutic or nutritional materials for treating disease or maintaining the vitality of the body.

In one aspect of the invention, a tissue culture medium is provided, comprising: at least 50% of water and a sterol compound that is dissolved in a fatty acid-containing oil at a concentration at least 0.1% by weight based on the weight of the oil and added to the water. The sterol compound preferably forms ester with the fatty acid in the oil under suitable conditions such as at high temperatures (e.g., >100° C.).

The concentration of the sterol compound in the oil preferably ranges from about 0.5% to 40% by weight, more preferably about 1% to 20% by weight, and most preferably about 2% to 6% by weight.

The fatty acid-containing oil is preferably vegetable oil, more preferably vegetable oil selected from the group consisting of corn oil, peanut oil, cottonseed oil, rice bran oil, safflower oil, tea tree oil, pine nut oil, macadamia nut oil, camellia seed oil, rose hip oil, sesame oil, olive oil, soybean oil and combinations thereof, and most preferably sesame oil.

The fatty-acid is preferably selected from the group consisting of palmitic acid, linoleic acid, oleic acid, trans-oleic acid, stearic acid, arachidic acid, and tetracosanoic acid.

According to this embodiment, the culture medium may further comprise wax that is dissolved in the fatty acid-containing oil and added to the water. The concentration of the wax preferably ranges from about 1% to 20% by weight, more preferably from about 2% to 10% by weight, and most preferably from about 3% to 6% by weight based on the weight of the oil.

The wax is preferably edible wax, more preferably edible wax selected from the group consisting of beeswax, castor-wax, glycowax, and carnaubawax, and most preferably beeswax.

Beeswax has long been used as an excipient for manufacturing drugs for external use. In traditional Chinese medicine, beeswax is a drug for detoxication, granulation promotion, for relieving pain and cardialgia and treating diarrhea, pus and bloody stool, threatened abortion with vaginal bleeding, septicemia, refractory ulcer and thermal injury ("A Dictionary of Chinese Materia Medica", in Chinese, "Zhong Yao Da Ci Dian", Science and Technology Press, Shanghai, 1986, page 2581).

The constituents of beeswax can be grouped into four categories, i.e., esters, free acids, free alcohols and paraffins. Beeswax also contains trace amount of essential oil and pigment. Among the esters, there are myricyl palmitate, myricyl cerotate, and myricyl hypogaeate. In free acids, there are cerotic acid, lignoceric acid, montanic acid, melissic acid, psyllic acid, hypogaeic acid and neocerotic acid. Among free alcohols, there are n-octacosanol and myricyl alcohol and in the paraffins, pentacosane, heptacosane, nonacosane and hentriacontane, and an olefin called melene. An aromatic substance called cerolein is also found in beeswax.

While not wishing to be bound to the theory, the inventor believes that the wax in the culture medium may provide structural support to the sterol compound dissolved in oil and allow the sterol compound to be slowly released to the medium. In addition, the wax may act like a sponge to absorb metabolic waste generated by the cells in the culture, further enhancing the active proliferation of the cells.

Optionally, the culture medium may further comprise propolis at a concentration ranging from about 0.1% to 30% by weight, more preferably from about 1% to 20% by weight, and most preferably from about 5% to 10% by weight based on the total weight of the oil.

Propolis is known as a sticky, gum-like substance which is used to build the beehives. In intact propolis a variety of trace ingredients in form of a homogenous mixture with resins, beeswax, essential oils and pollens as predominant ingredients, as well as other ingredients such as flavonoids and phenol carboxylic acids. Natural propolis hardly dissolves in water and has a peculiar odor. Propolis can be prepared from beehives by extraction with organic solvents such as ethonol, ether and chloroform.

In another aspect of the invention, a method for culturing potentially regenerative cells in vitro is provided. The method comprises: isolating tissue cells or tissues from a predetermined site of the body of a live mammal; and culturing the isolated tissue cells or tissues a culture medium under suitable conditions such that potentially regenerative cells contained in the isolated tissue cells or cells migrated from the isolated tissues are activated to continuously proliferate and differentiate to form a tissue-organ which shares substantially the same physiological structure and at least one physiological function with that of the corresponding tissue in situ and in vivo.

The mammal may be a rodent, a primate or a human, preferably a primate, more preferably a human, and most preferably an adult human. The isolated tissue cells or tissues may be isolated from any site of the body of the mammal, for example, the brain, heart, liver, lung, intestine, stomach, kidney, bone marrow, and skin. The isolated tissue cells are not embryonic stem cells, and the isolated tissue is not from the blastocyst of the mammal.

The culture medium may comprise at least 50% of water and a sterol compound that is dissolved in a fatty acid-containing oil at a concentration at least 0.1% by weight based on the weight of the oil and added to the water. The sterol compound preferably forms ester with the fatty acid in the oil under suitable conditions such as at high temperatures (e.g., >100° C.).

The potentially regenerative cells contained in the isolated tissue cells or tissue may be activated in the culture medium to continuously proliferate and differentiate for at least 5 days, preferably for at least 10 days, more preferably for at least 30 days, and most preferably for at least 50 days.

The tissue-organ formed in the culture shares at least one physiological function with that of the tissue in situ and in vivo, for example, the ability to produce molecules with biological activities such as enzymatic activity, signaling and regulatory functions, and the ability to cause muscle contraction in response to electric current.

For example, a viable explant of tissue from a specific organ of an animal (e.g., a mouse) can be obtained by surgery. The explant is washed with proper buffer (e.g., PBS containing antibiotics) under sterile conditions, cut into small pieces (e.g., 1 mm×1 mm) and placed in culture plates with suitable sizes (e.g., 6-well, 24-well and 96-well culture plates), preferably with tissue pieces separated from each other in the plates. A regular culture medium (e.g., 0.5 ml of MEM) can be added to the culture, for example, from the edge of the plate in order not to disturb the tissue pieces, and the tissue culture is incubated under proper conditions (e.g., in a 37° C., 5% $CO_2$ incubator) for 1–2 hr. The cell growth regulator of the present invention is then added to the plates, the mixture of the cell growth regulator and the regular culture medium constituting an embodiment of the tissue culture medium of the present invention. Under the regenerative conditions provided by the tissue culture medium of the present invention, the PRCs contained in the tissue pieces can migrate from the original tissue, actively proliferate and directional differentiate to generate new tissue and tissue-organ with substantially the same physiological structure and function as the one existing in vivo and in situ.

Optionally, the tissue explants may be homogenized and digested with proper enzymes (e.g., trypsin and collagenase) to produce single cells. The cells can be separated from the digestive solution and undigested tissues, washed and incubated in the tissue culture medium of the present invention under conditions (e.g., 37° C., 5% $CO_2$). Under the regenerative conditions provided by the tissue culture medium of the present invention, the PRCs among the single cells isolated from the tissue explants can actively proliferate and directional differentiate to generate new tissue and tissue-organ with substantially the same physiological structure and function as the one existing in vivo and in situ.

According to any of the above embodiments, the sterol compound may be an animal sterol or a plant sterol (also called phytosterol). Examples of animal sterol include cholesterol and all natural or synthesized, isomeric forms and derivatives thereof. Preferably, the sterol compound is selected from the group consisting of stigmasterol, campesterol, β-sitosterol, chalinosterol, clionasterol, brassicasterol, α-spinasterol, daucosterol, avenasterol, cycloartenol, desmosterol, poriferasterol, and all natural or synthesized, isomeric forms and derivatives thereof. More preferably, the sterol compound is a combination of stigmasterol, β-sitosterol, and campesterol, collectively referred to herein as "sitosterol".

Optionally, the sterol compound is a combination of stigmasterol and β-sitosterol.

Also optionally, the sterol compound is a combination of brassicasterol and β-sitosterol.

Also optionally, the sterol compound is a combination of brassicasterol, stigmasterol and β-sitosterol.

Also optionally, the sterol compound is a combination of campesterol, stigmasterol and β-sitosterol.

It is to be understood that modifications to the sterol compound i.e. to include side chains also fall within the purview of this invention. It is also to be understood that this invention is not limited to any particular combination of sterols forming a composition.

It is to be understood that modifications to the sterol compound i.e. to include side chains also fall within the purview of this invention. It is also to be understood that this invention is not limited to any particular combination of sterols forming a composition. In other words, any sterol compound alone or in combination with other sterol compound in varying ratios as required depending on the nature of the ultimate formulation fall with the purview of this invention.

The sterol compound for use in this invention may be procured from a variety of natural sources. For example, phytosterol may be obtained from the processing of plant oils (including aquatic plants) such as corn oil, wheat germ oil, soy extract, rice extract, rice bran, rapeseed oil, sesame oil, and other vegetable oils, and fish oil. Without limiting the generality of the foregoing, it is to be understood that there are other sources of phytosterols such as marine animals from which the composition of the present invention may be prepared. For example, phytosterols may be prepared from vegetable oil sludge using solvents such as methanol. Alternatively, phytosterols may be obtained from tall oil pitch or soap, by-products of the forestry practice.

Although not wishing to be bound by the theory as to the mechanism of action of the sterol compound in activation of the PRCs, the inventor believes that the sterol compound may play important roles in inducing morphogenesis of the cells by changing the fluidity and permeability of the cell membrane. As a result, many cell membrane-associated proteins such as kinases and phosphotases may be activated to stimulate cell growth. It is also plausible that dormant PRCs may be activated due to morphogenic changes in the membrane. Further, differentiated adult tissue cells may also be induced to undergo transformation into a non-differentiated phenotype, i.e., the process called "dedifferentiation". With the change of permeability of the cell membrane, other mitogens and regulatory molecules may be more readily uptaken by the cells so as to stimulate a balanced growth of a wide variety of cells needed for physiological tissue repair and functional organ regeneration. Moreover, expression and phosphorylation of cell adhesion molecules (CAMs) may be stimulated, presumably due to activation of membrane-bound proteins during the morphogenesis process, thus further enhancing association of cognate cells to form a specific tissue, and assembly of cognate tissues to form a functional tissue-organ in the cell culture.

According to any of the above embodiments, the culture medium may further comprise baicalin dissolved in the oil, preferably at a concentration ranging from about 0.001 to 2% by weight, more preferably about 0.02 to 1% by weight, and most preferably about 0.02% to 0.5% by weight based on the total weight of the oil.

Baicalin may have anti-inflammatory effects on the cells, which helps providing a low inflammation environment for the cloning of tissue-organ in the culture. It might also be possible that baicalin might bind to cell membrane receptors for polysaccharides such as selectin and further promote cell adhesion.

Baicalin may be obtained by extracting huangqin (*Scutellaria baicalensis Georgi*) in oil, alcohol or other organic solvent, preferably in oil at temperature higher than 100° C., more preferably between about 120–200° C., and most preferably between about 160–180° C. Preferably, the root of huangqin is used and may be obtained from the plant selected from one or more members of the group of *Scutellaria viscidula Bge, Scutellaria amoena C. H. Wright, Scutellaria rehderiana Diels, Scutellaria ikonnikovii Juz, Scutellaria likiangensis Diels* and *Scutellaria hypericifolia Levl* of Labiatae Family. Dictionary of Chinese Materia Medica, Shanghai Science and Technology Press, 1988, pages 2017 to 2021.

According to any of the above embodiments, the oil in the culture medium is an oil-extract of huangqin wherein the amount of huangqin is 2–60% by weight based on the total weight of the oil.

Also according to any of the above embodiments, the culture medium may further comprise obaculactone dissolved in the oil, preferably at a concentration ranging from about 0.001 to 2% by weight, more preferably about 0.02 to 1% by weight, and most preferably about 0.02% to 0.5% by weight based on the total weight of the oil.

Obaculactone is also called limonaic acid and may be obtained by extracting huangbai (*Phellodendron amurense Rupr*) in oil, alcohol or other organic solvent, preferably in oil at temperature higher than 100° C., more preferably between about 120–200° C., and most preferably between about 160–180° C. Alternatively, obaculactone may also be obtained by extracting huangbai in alcohol such as ethanol. Preferably, the bark of huangbai is used and may be obtained from the plant selected from one or more members of the group of *Phellodendron chinense Schneid, Plellodendron chinense Scheid* var. *glabriusculum Schneid, Phellodendron chinense Schneid* var. *omeiense Huang, Phellodendron Schneid* var. *yunnanense Huang* and *Phellodendron chinense Schneid* var. *falcutum Huang*. A Dictionary of Chinese Materia Medica, Shanghai Science and Technology Press, 1988, pages 2031 to 2035.

According to any of the above embodiments, the oil in the culture medium is an oil-extract of huangbai wherein the amount of huangqin is 2–60% by weight based on the total weight of the oil.

Optionally, the culture medium may further comprise obabenine, preferably at a concentration ranging from about 0.001% to 2% by weight, more preferably about 0.002% to 0.5% by weight, and most preferably about 0.003% to 0.1% by weight based on the total weight of the oil.

Optionally, the inventive composition may further comprise obabenine, preferably at a concentration ranging from about 0.001% to 2% by weight, more preferably about 0.002% to 0.5% by weight, and most preferably about 0.003% to 0.1% by weight.

Obabenine may be obtained by extracting huangqin, huangbai, and/or huanglian (*coptis chinensis Franch*) in oil, alcohol or other organic solvent. Root of huanglian is preferably used. Huanglian may be selected one or more from the group of *Coptis deltoidea* C. Y. Cheng et Hsiao, *Coptis omeiensis* (Chen) C. Y. Cheng, and *Coptis teetoides* C. Y. Cheng of Ranunculaceae Family. A Dictionary of Chinese Materia Medica, Shanghai Science and Technology Press, 1988, pages 2022 to 2030.

According to any of the above embodiments, the oil in the culture medium is an oil-extract of huanglian wherein the amount of huangqin is 2–60% by weight based on the total weight of the oil.

Also optionally, the culture medium may further comprise berberine, preferably at a concentration ranging from about 0.001% to 2% by weight, more preferably about 0.002% to 0.5% by weight, and most preferably about 0.003% to 0.1% by weight based on the total weight of the oil.

Also optionally, the culture medium may further comprise narcotoline, preferably at a concentration ranging from about 0.001% to 2% by weight, more preferably about 0.002% to 0.5% by weight, and most preferably about 0.003% to 0.1% by weight based on the total weight of the oil.

In a particular embodiment, the oil in the culture medium is an oil-extract of huangqin containing baicalin at a concentration ranging from about 0.001 to 2% by weight based on the total weight of the oil, wherein the sterol compound is a phytosterol and the oil is sesame oil.

Also optionally, the oil in the culture medium is an oil-extract of heshouwu wherein the amount of heshouwu is 2–60% by weight based on the total weight of the oil.

Also optionally, the inventive composition may further comprise an extract of heshouwu (*Polygonum multiflorum Thunb* which belongs to the family of Polygonacea), preferably the root tuber of heshouwu (*Radix polygoni multiflori*). Its common name in English-speaking countries is Fleeceflower Root and is known in China as Heshouwu, Shouwu, or Chishouwu.

Heshouwu can be harvested in autumn and winter when leaves wither, washed clean, and the large one cut into pieces, and then dried to produce a dried heshouwu. Heshouwu can also be prepared by steaming (e.g., for 3 hr) to produce a steamed heshouwu, optionally in the presence of wine to produced the so-called wine-processed heshouwu. The slices or pieces of heshouwu may be mixed with thoroughly with black bean juice and stewed in a suitable non-ferrous container until the juice is exhausted. The mixture is dried to solidify and then cut into slices to produce the so-called prepared heshouwu.

Crude heshouwu and prepared heshouwu may differ in the composition. It is known that all kinds of heshouwu contain free phosphatidylcholine (lecithin), phosphatidylinositol, phosphatidylcholine, phosphatidylethanolamine (cephalin), N-free phosphatidylethanolamine and sphingolipids. Crude heshouwu usually contains 3.7% phospholipids, and higher than processed heshouwu. Heshouwu also contains emodins such as anthraquinones or anthrones which mainly glycoside with glucose and rhamnose to form mono- or di-glycoside, chrysophanol, emodin, rhein, chrysophanol ester, and chrysophanin acid anthrone. Processed heshouwu has a lower concentration of anthraquinones. Heshouwu also contains tetrahydroxystilbene glycoside and its analogues, and the processed heshouwu have slight higher concentration. Heshouwu is abundant of trace elements, such as calcium, iron, manganese, copper, and zinc at a concentration of about 421 ug/g, tens times higher than most herb. In addition, heshouwu has high concentration of starch, soluble amylose, vitamins, amino acids, and coarse fat.

Also optionally, the culture medium may further comprise various amino acids, preferably all 20 natural amino acids (e.g., alanine, asparagines, aspartic acid, cysteine, glutamic acid, glutamine, glycine, phenylalanine, histidine, isoleucine, lysine, leucine, methionine, proline, arginine, serine, threonine, valine, tryptophan, and tyrosine), for providing nutrition support to cell growth. The amino acids may be chemically synthesized or obtained from natural sources. For example, a full spectrum of natural amino acids may be obtained by extracting earthworms, a rich source of protein/amino acids, in oil or alcohol.

The culture medium may further comprise nucleic acid bases such as adenine, cytidine, guanine, thymine and uridine.

In a particular embodiment, the oil in the culture medium is an oil-extract of earthworm wherein the amount of earthworm is 2–60% by weight based on the total weight of the oil.

The tissue culture medium may further include a regular tissue culture medium such as DMEM, MEM, etc.

The tissue culture medium may further comprise some or all of the compositions of a typical medium suitable for the cultivation of mammalian cells. Examples of these reagents for tissue culture include, but are not limited to, a) Amino acids such as arginine, cystine, glutamine, histidine, isoleusine, leucine, lysine, methionine, phenylalanine, threonine, tryptophan, tyrosine, and valine; b) Vitamins such as biotin, choline, folate, nicotinamide, pantothenate, pyridoxal, thiamine, and riboflavin; c) Salts such as NaCl, KCl, $NaH_2PO_4$, $NaHCO_3$, $CaCl_2$, and $MgCl_2$, d) Proteins such as insulin, transferrin, specific growth factors; and e) Miscellaneous: glucose, penicillin, streptomycin, phenol red, whole serum.

In yet another aspect of the invention, isolated potentially regenerative cells from a predetermined site of the body of a live mammal are provided. The isolated potentially regenerative cells, when cultured in a culture medium under suitable conditions, are capable of being activated to continuously proliferate and differentiate to form a tissue-organ which shares substantially the same physiological structure and at least one physiological function with that of the corresponding tissue in situ and in vivo.

The potentially regenerative cells may be isolated from any site of the body of the mammal such as an adult body of a human, for example, the brain, heart, liver, lung, intestine, stomach, kidney, bone marrow, and skin. The isolated potentially regenerative cells are not embryonic stem cells, and are not from the blastocyst of the mammal.

The culture medium may comprise at least 50% of water and a sterol compound that is dissolved in a fatty acid-containing oil at a concentration at least 0.1% by weight based on the weight of the oil and added to the water. The sterol compound preferably forms ester with the fatty acid in the oil under suitable conditions such as at high temperatures (e.g., >100° C.).

The isolated potentially regenerative cells, when cultured in the culture medium, may be able to continuously proliferate and differentiate for at least 5 days, preferably for at least 10 days, more preferably for at least 30 days, and most preferably for at least 50 days.

The compositions and methods of the present invention can be utilized to generate in vitro a large amount of regenerative cells, tissues and/or organs with normal physiological structure and function. These biological materials can serve as extremely valuable models for basic scientific investigation in every aspect of life sciences, and be utilized in many practical applications such as nutraceutical discovery, drug screening, pharmacokinetics studies, medical devices and tissue/organ transplantation.

EXAMPLES

Example 1

Culture of Human Intestinal Cells in Vitro

An in vitro experiment on human intestinal cells was carried out by following this protocol:

Obtained normal human living intestine from surgical operations, first put the tissue lump into double antibiotics (penicillin and streptomycin)-containing, precooled phosphate buffered saline (PBS), rinsed three times, cut the large tissue lump into small pieces of 1 $mm^3$, then rinsed them with same PBS two times, put these washed small pieces into 0.25% trypsin or 1% collagenase digestive solution prepared with sterile PBS, digested them under the condition of 4° C. overnight with shaking (about 16 hours) or 37° C. water bath, 3 hours with shaking.

Used pipette or aspirator to blow and aspirate the tissue repeatedly or poured the mixture of tissue pieces with enzyme solution into stainless steel filter, and used syringe plug to grind the tissue pieces until all pieces were dispersed into single cells.

Seated still the mixture of single cells and enzyme solution (e.g. trypsin or collagenase, known to skilled artisans in this field) for 5 minutes. Discarded the undigested and precipitated large pieces and indigestible connective tissues, moved the supernatant containing large amount of cells and digestive enzyme to another centrifuge tube, and if necessary, filtered the supernatant with stainless steel filter.

Centrifuged the supernatant at 4° C., 1500 rotations per minute (rpm) for 5 min, discarded the supernatant containing digestive enzyme, added small amount of PBS, vortexed, and then added more precooled PBS and mixed.

Centrifuged the supernatant at 4° C., 1500 rpm for 5 min, discarded the supernatant, added small quantified amount of precooled PBS, vortexed and added more quantified amount of precooled PBS, mixed and counted the cell number.

Centrifuged the supernatant at 4° C., 1500 rpm for 5 min, discarded the supernatant, added small quantified amount of 15% newborn calf serum(NCS) MEM medium or RPMI 1640 medium, vortexed and added more appropriately quantified amount of medium, adjusted cell concentration to $1 \times 10^5$ cells/ml, mixed.

Dispensed the cell suspension into wells of multi-well plates (96 wells, 24 wells, 12 wells or 6 wells) precoated with rat tail collagen. 200 µl per well for 96-well plate, 1 ml for 24-well plate, 2 ml for 12-well plate, and 4 ml for 6-well plates.

Cultured the cells in 37° C., 5% $CO_2$ incubator or in 37° C., 5% $CO_2$ and 45% $O_2$ incubator. 24 hours later, all the cells attached to well bottom and grew well. Divided the wells into two groups: test group and control group. In test group wells, 15% fetal calf serum (FCS) MEM medium or 15% FCS RPMI 1640 medium plus sitosterol (0.2% w/w) was added.

Choice of regular tissue culture medium (e.g. MEM, DMEM, RPMI) is known to skilled artisans in the art. Only regular tissue culture medium was added into the control group wells. In the test group, the tissue culture medium contains 10 grams of the inventive cell growth regulator per 100 ml medium.

Changed the medium according to the routine protocol, i.e., discarded half of the old medium and added same amount of fresh medium, e.g., 15% FCS MEM medium or 15% FCS RPMI 1640 medium, from then on, changed the medium every three days, observed cells regularly.

After 55 days of culture, as in FIG. 1, mucosal tissue cells appeared in different forms, all cells lived vigorously in the medium and some were dividing, In these live cells, some proliferated persistently and are termed herein potentially regenerative cells (PRCs), but some did not have these characteristics.

Figure 2:
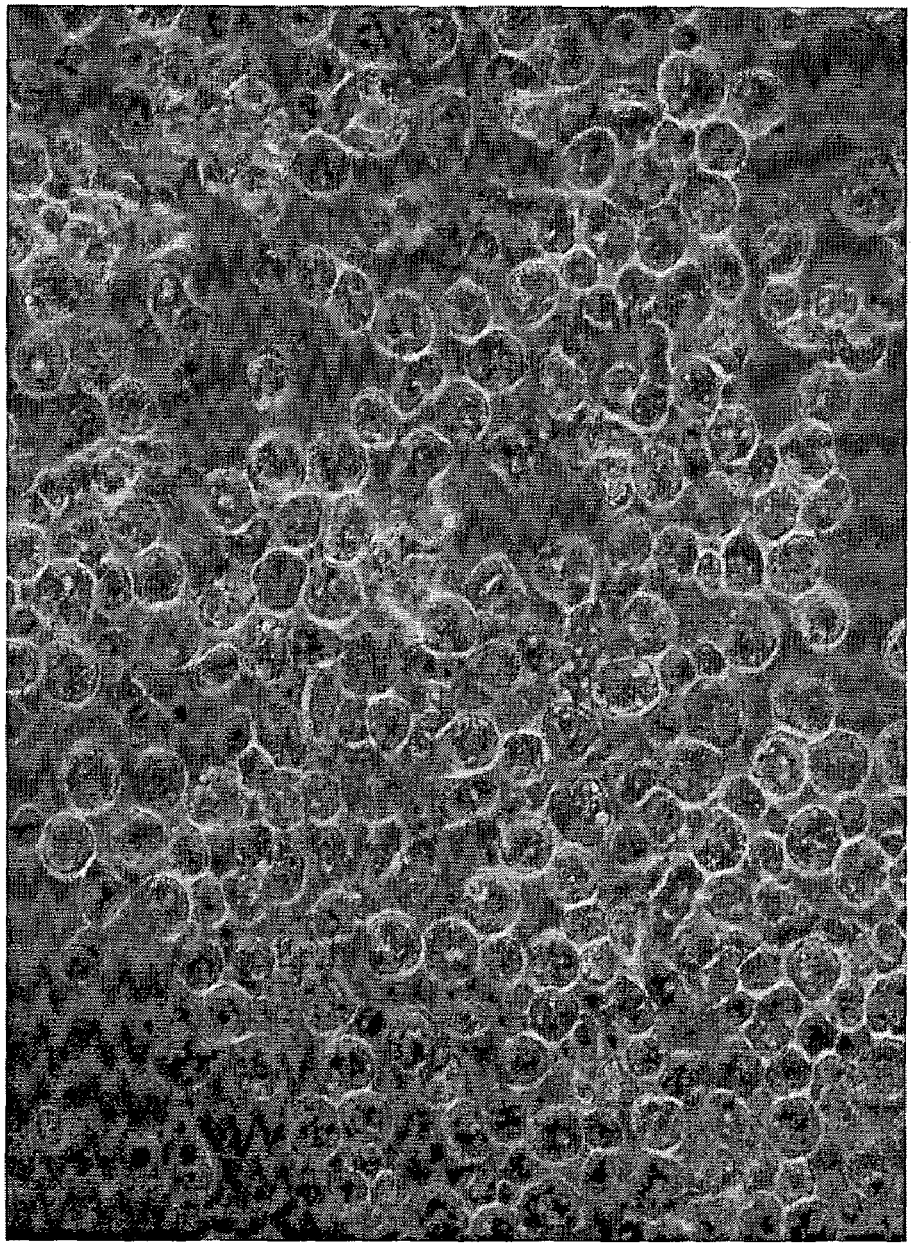
FIG. 2 shows active proliferation of human intestinal cells that are PRCs in the culture.

Refer to FIG. 2. The large dividing cells were from PRCs of replicating tissues and organs, the small, non-dividing cells were non-dividing, preexisting PRCs, and newly created PRCs. These PRCs proliferated continuously in the medium under the effect of the inventive cell growth regulator, manifesting typical characteristics of stem cells. After examination of cellular function, they can be used as in vitro experimental models for studies on normal cell structure and function.

Figure 3:
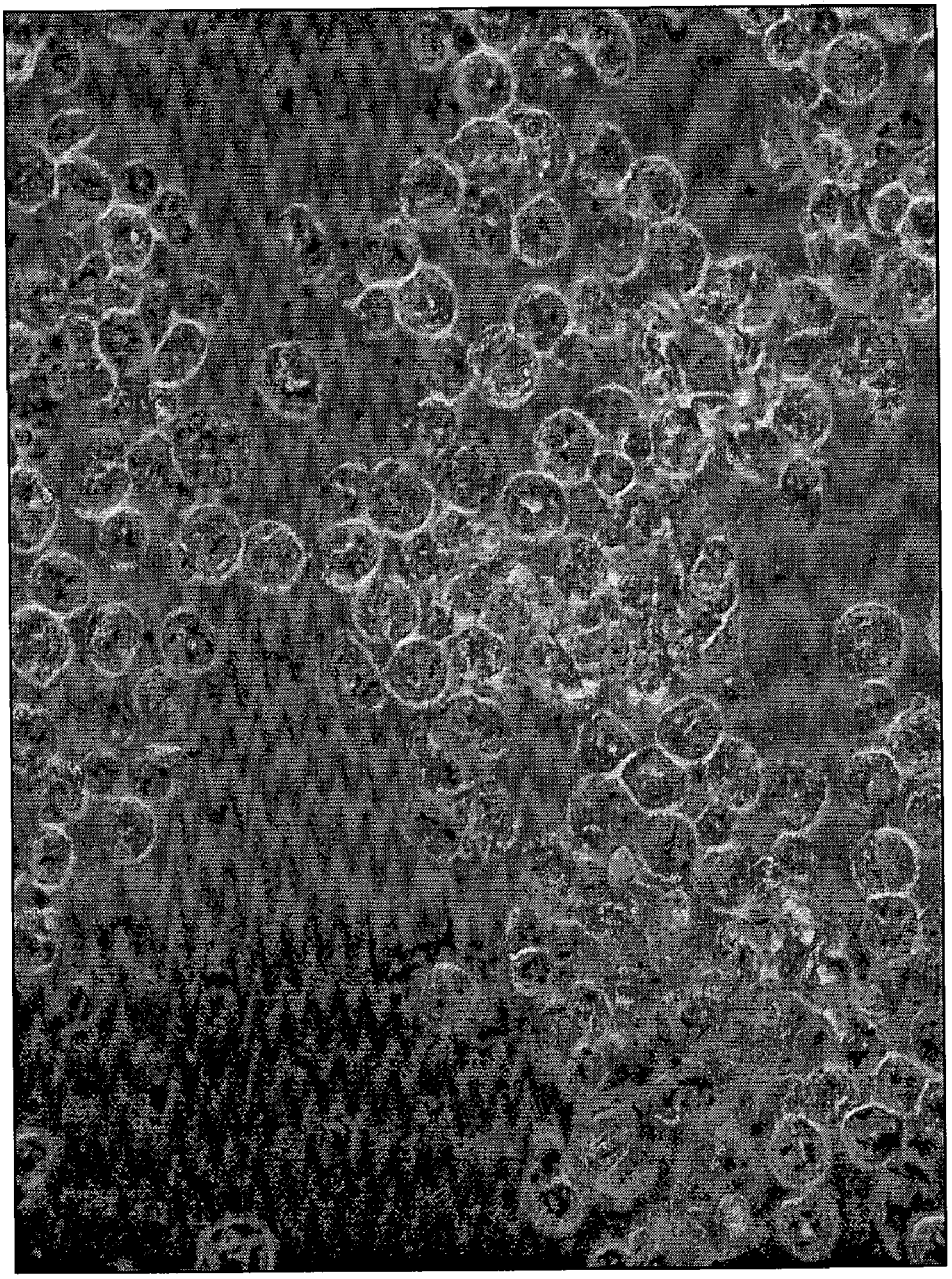
FIG. 3 shows that some of the cloned human intestinal cells adhere to each other to form primary tissues.

Refer to FIG. 3. Some of the persistently proliferating cells in the medium began to link and form tissues, the cells in the newly formed tissues changed from a round form to a tissue-specific form. Some of the cells still proliferated continuously. The tissues they formed can be used as in vitro experimental models for studies on normal tissue structure and function.

Figure 4:
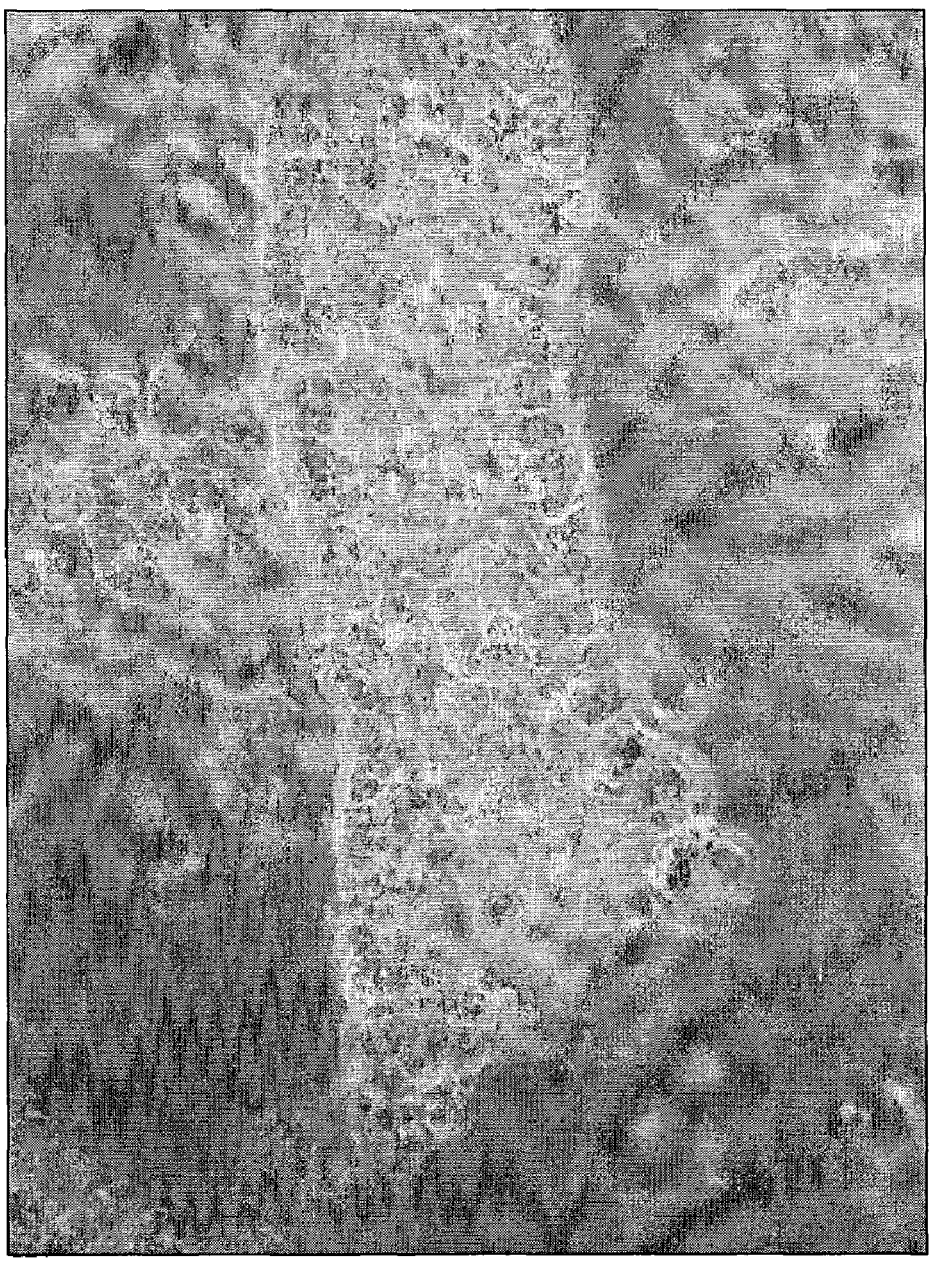
FIG. 4 shows that the primary tissues assemble to form villi of the intestinal mucosa.

Refer to FIG. 4. After proliferating cells linked and formed primary tissues, the latter continued to assemble into fully developed tissues, e.g., villi of intestinal mucosa, following the predetermined genetic program of the PRCs.

In the course of above-mentioned research in which cells evolved into tissues and organs in vitro, the inventor investigated the source of the cells with the stem cell-like proliferating ability. It was observed under microscope that some of the growing single cells began to divide, become terminally differentiated cells, and did not form new tissues, whereas other cells proliferated persistently and formed new tissues with different forms, and several of different forms of tissues assembled and formed large tissues and organs.

To find out the reason, the inventor fluorescently labeled both the cells with proliferation potential and the proliferating cells derived from asymmetrical division of proliferating cells. The results indicated that the cells in both groups shared identical markers, suggesting that the source cells of tissue regeneration may be the non-proliferating cells derived from the asymmetrical division of proliferating cells. These non-proliferating cells are termed "Potentially Regenerative Cells" (PRCs). These cells might be duplicates of cells left over in every stage of development and tissue regeneration; and they carried all of the information specific to that stage. Together with tissues cells directly from the cell proliferation, PRCs formed tissues or organs and appear to be the same as regular tissue cells morphologically.

However, when adult tissues or organs are injured, dysfunctional or degenerated, the PRCs are activated, divide and proliferate in situ and form new tissues and organs to compensate for the functional and structural defects. The developmental process of PRCs is illustrated in FIG. 5.

Example 2

Culture of Mouse Intestinal Mucosal Villi in Vitro

The in vitro experiment on mouse intestinal cells was carried out by following this protocol:

Killed Kunming mouse provided by qualified Laboratory Animal Institute, Chinese Academy of Medical Sciences with routine protocol known to skilled artisans in this field. Sterilized its body surface two times with 75% ethanol, 5 minutes each time. According to anatomical localization, took the exact living tissues. To disperse the tissues into single cells, put the tissue pieces into double antibiotics (penicillin and streptomycin)-containing, precooled PBS, rinsed three times, cut the large tissue lump into small pieces of 1 mm$^3$, then rinsed them with the same PBS two times, put these washed small pieces into 0.25% trypsin or 1% collagenase digestive solution prepared with sterile PBS, digested them under the condition of 4° C. overnight with shaking (about 16 hours) or 37° C. water bath, 3 hours with shaking.

Cultured with the same method as in Example 1, the difference was that small explants of proximal intestine from fetus Kunming mice were used in this example. In the test group, 5 to 10 explants were planted in each multi-well plate containing the inventive culture medium. Cultured the attached explants with an interval of 1 mm between two explants. According to total weight of medium in each well, sitosterol of 1% (w/w), beeswax of 5% (w/w), and optionally propolis of 5% (w/w) could be added as cell growth regulators based on the total weight of the cell growth regulator. The concentration of cell growth regulators was of 20 grams per 100 ml medium.

The same explants were used in the control group, but no above-mentioned cell growth regulator was added in control wells. Other conditions were the same as in test group. Cultured both groups according to routine protocols.

Refer to FIG. 6. Through continuous culture for 30 days, explants in test group attached to the well bottom and grew very well, but those in control group began to detach from the bottom of the wells.

Figure 8:
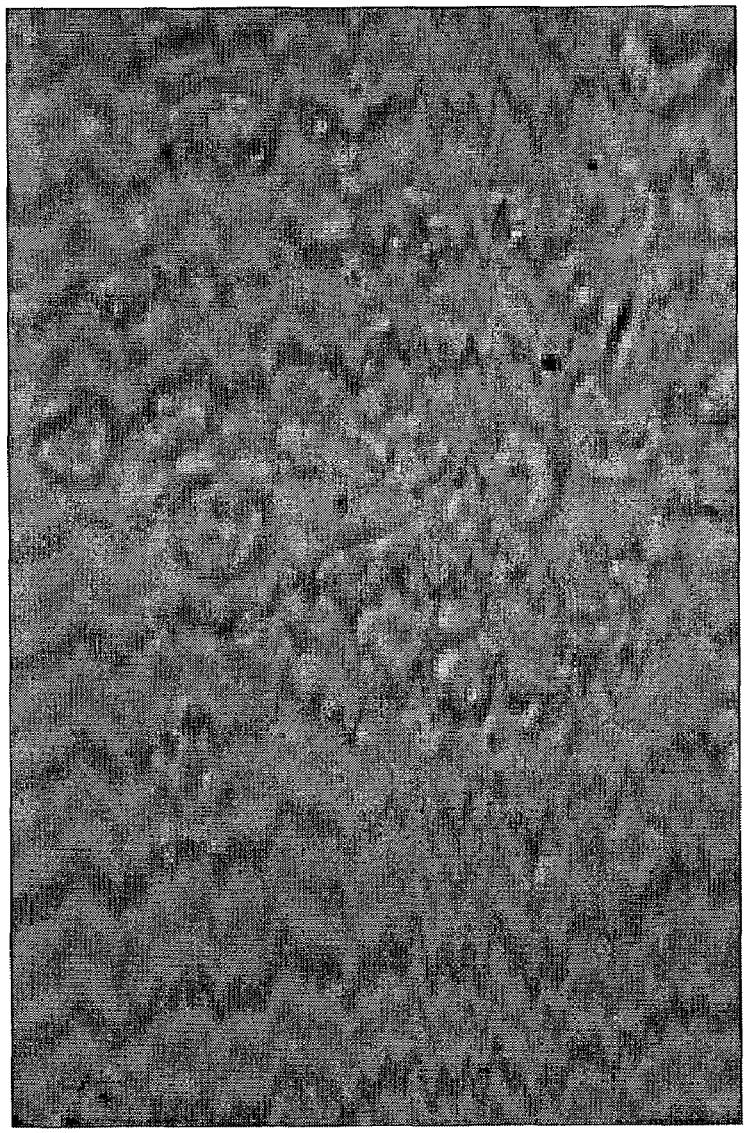
FIG. 8 shows that single cells migrated from the explants proliferated to form clones of cells.

Refer to FIG. 7. Through continuous culture for 60 days, in the test group, the intestinal explants continued to live, cells appeared to be separated from the tissues. Single cells were observed to suspend in the medium. In contrast, in the control group, intestinal explants began to degenerate and die and the isolated cells in a small number also began to die. With continuous culture in the inventive culture medium, the single cells in the test group began to form clones(FIG. 8).

Refer to FIG. 9. Continued to culture intestinal cells in the test group. It was observed that the cells began to aggregate and adhere to each other. These connected cells formed primary tissues, and the latter expanded and formed intestinal mucosal tissues.

Refer to FIG. 10 showing the ends of intestinal villi which was formed at the last stage of the development. The amplified intestinal mucosa were also shown.

Figure 11A:
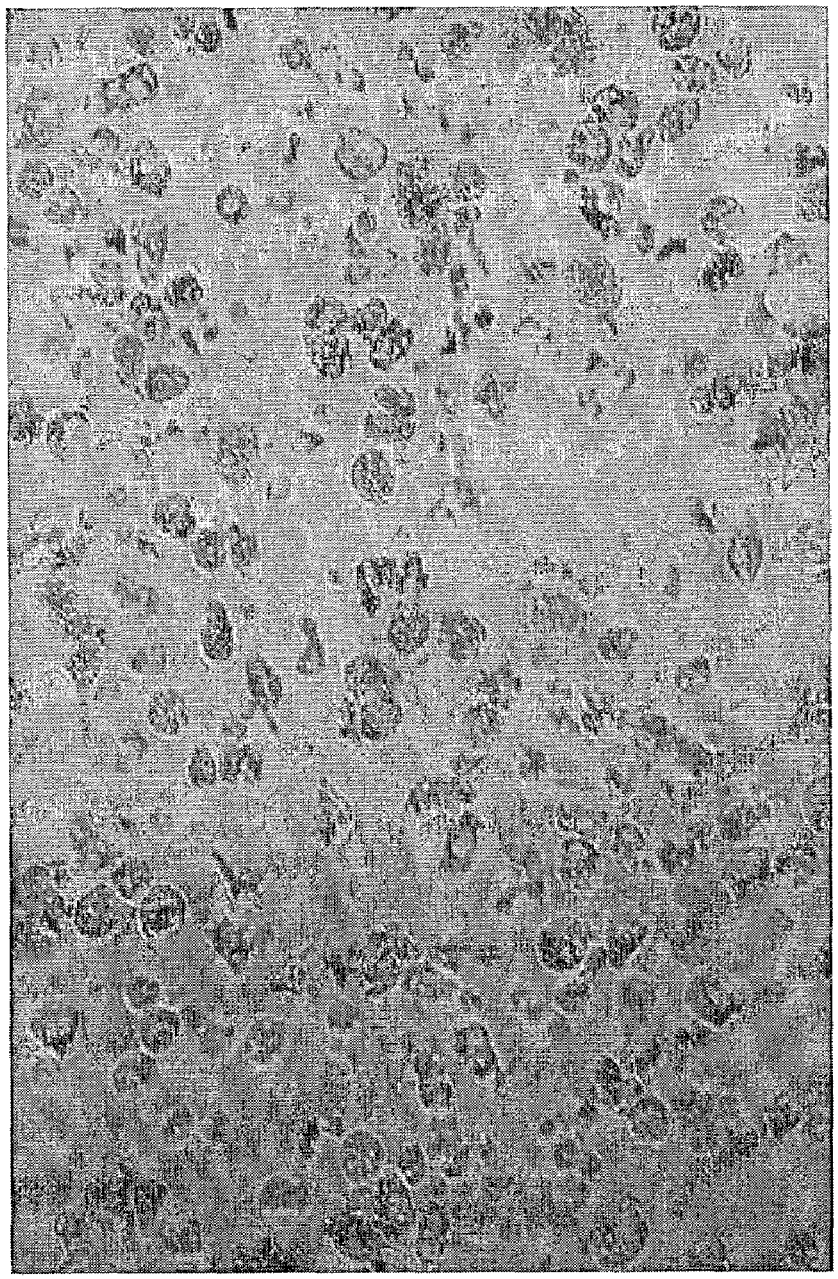
FIG. 11A shows migration of single cells from explants of mouse intestine.
Figure 11B:
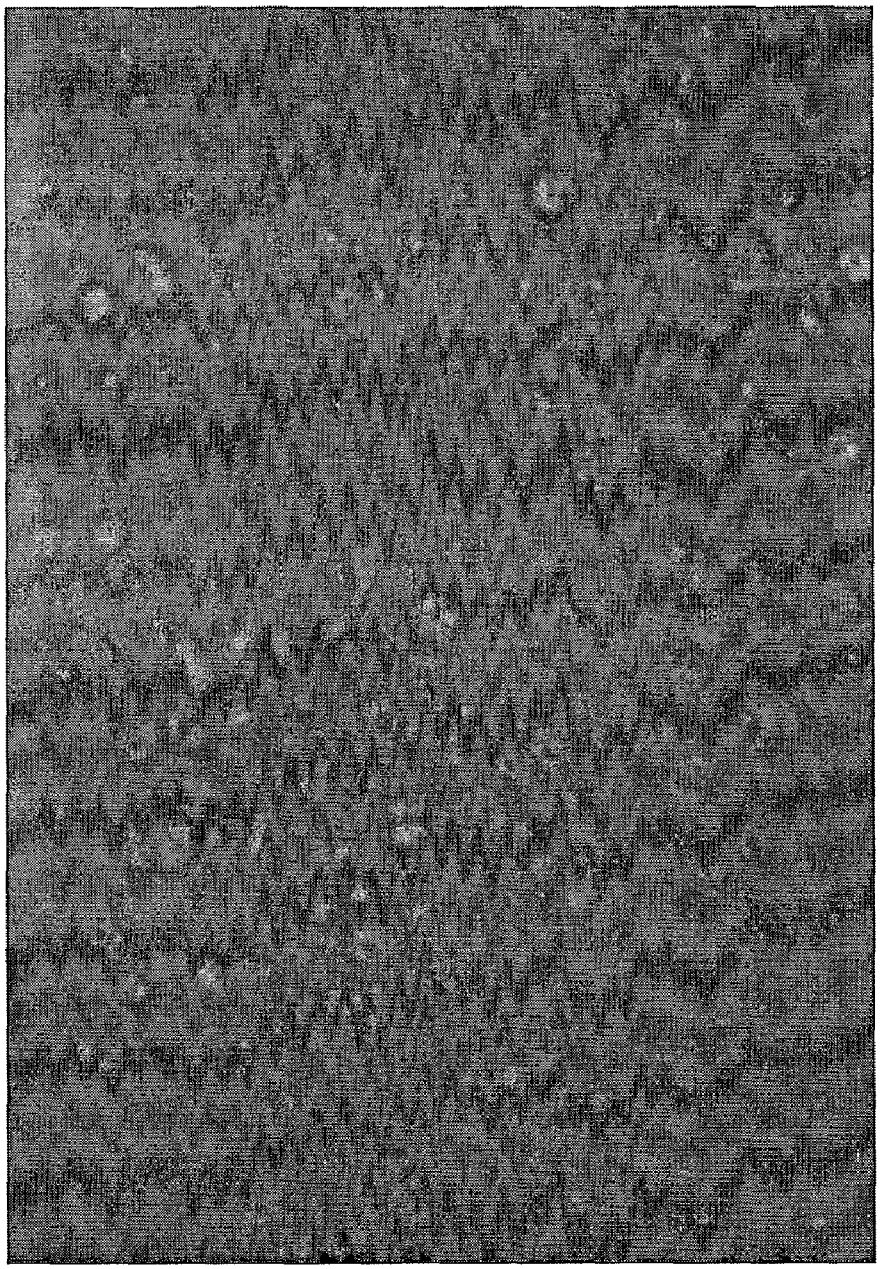
FIG. 11B shows that the migrated single cells from explants of mouse intestine proliferated in the culture to form primary intestinal tissue.
Figure 12A:
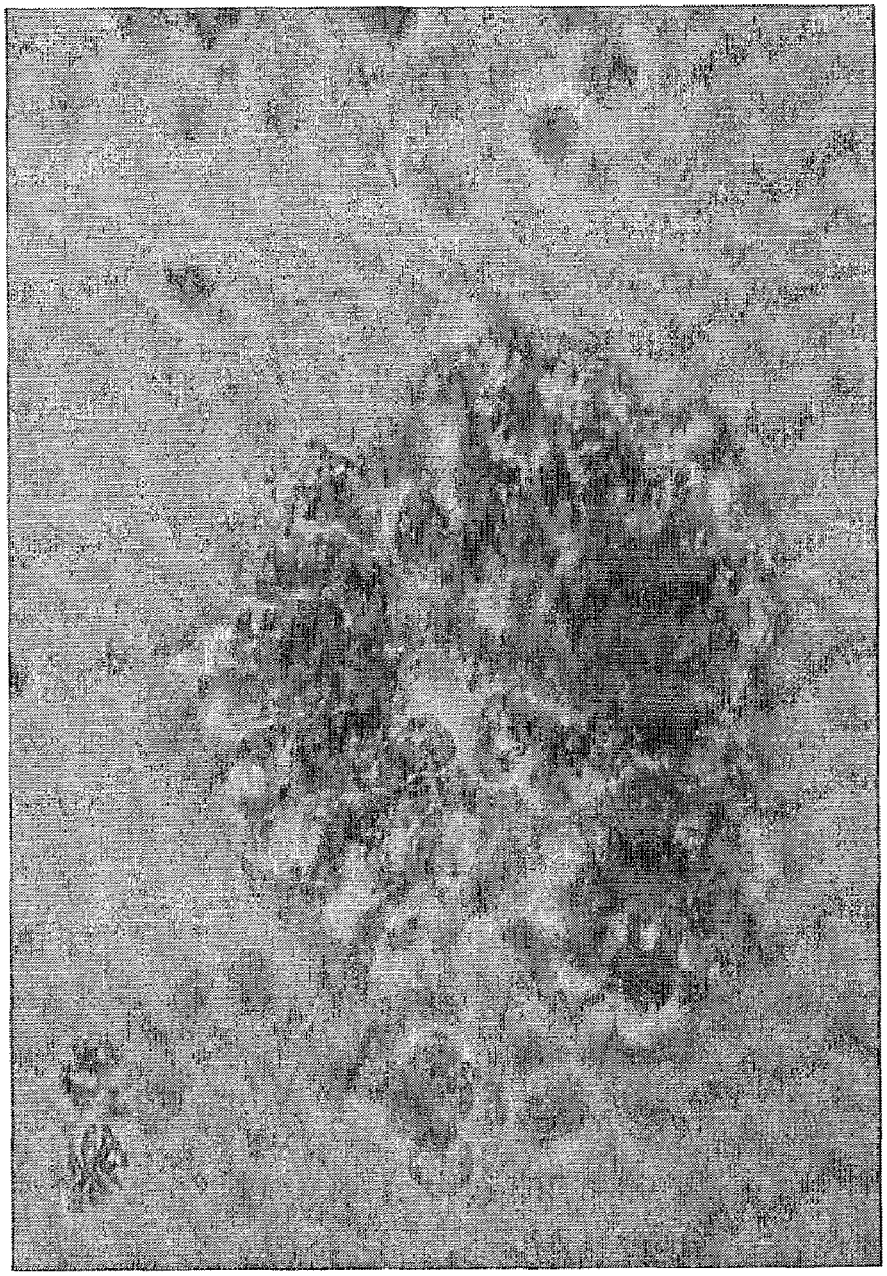
FIG. 12A shows adhesion of cells to form the basic structure of an intestinal villus.
Figure 12B:
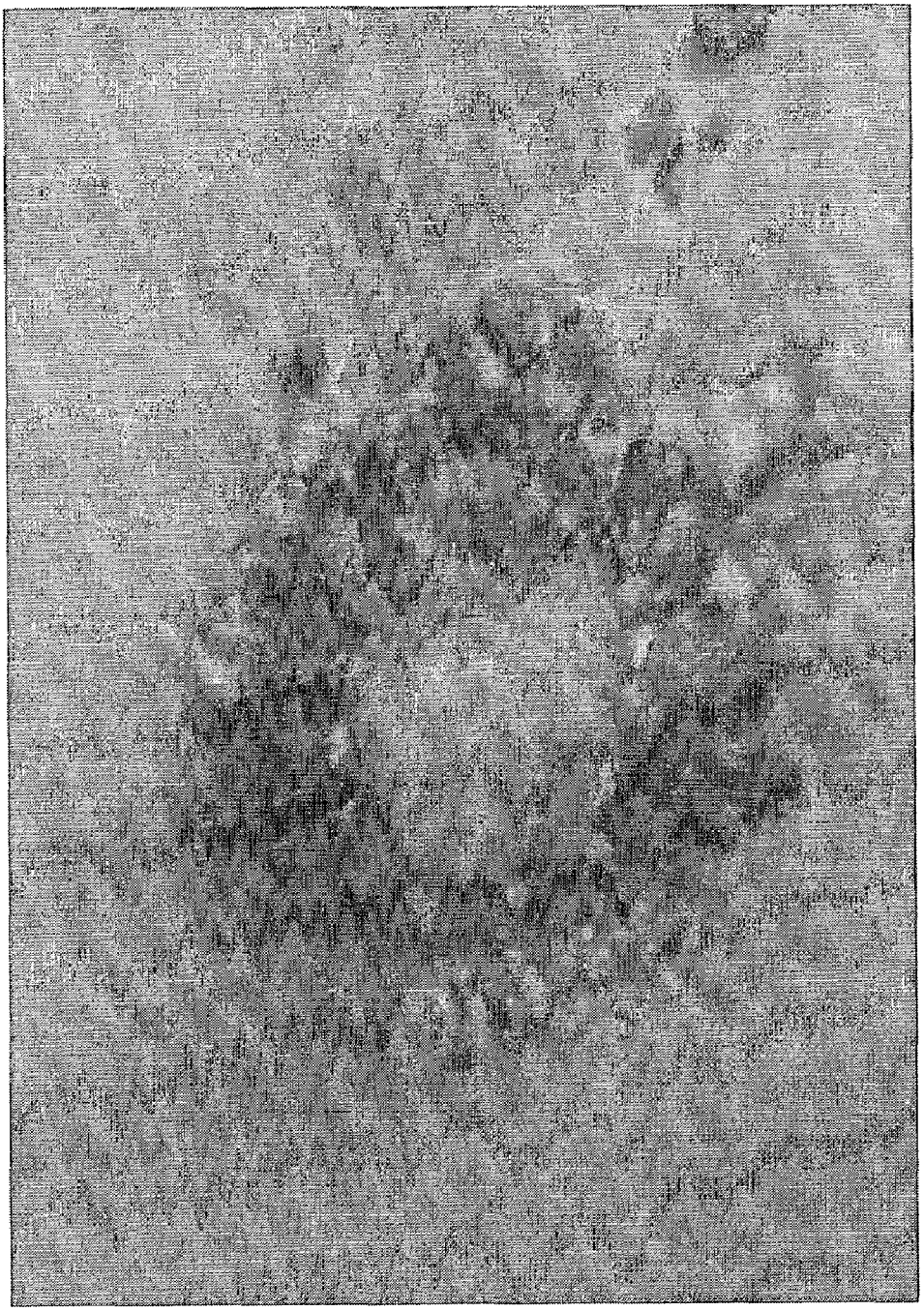
FIG. 12B shows that a complete basic structure of an intestinal villus is formed in the culture.

Through above-mentioned culture process, single cells were observed to migrate from tissue explants and into the surrounding medium (FIG. 11A). A large number of intestinal single cells in different forms appear in the culture, and these single cells continued to proliferate and began to form primary tissues (FIG. 11B). These primary tissues aggregated step by step, and integrated with each other to form tissues with basic functions (FIG. 12a). As shown in FIG. 12A, it is obvious that there were cell-cell adhesion, tissue-tissue connection and tissue movement for connection. In FIG. 12B, formation of tissues with physiological structures could be found, including structures resembling the cross-sections of the intestinal villus bases, cells linking with each other to form a circle, and scattered cells approaching these tissues to surround the villi.

Figure 13:
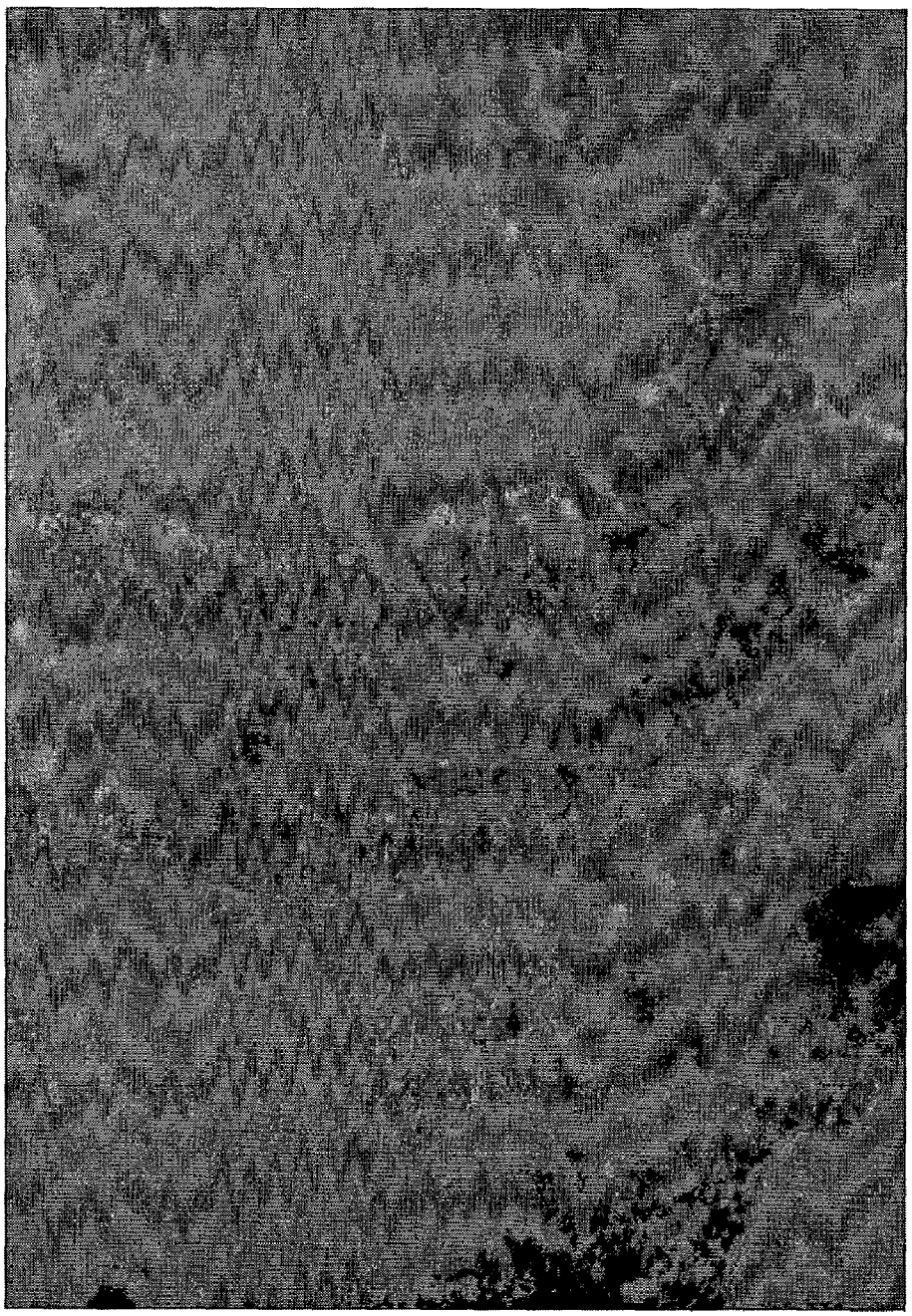
FIG. 13 shows that an intestinal villus is cloned in the culture.

Refer to FIG. 13. Through culturing, intestinal cells from mouse explants began to form the villus organ. It can be seen that the cells replicated along the basic circle of villi, eventually formed new intestinal villi and completed the cloning of intestinal mucosa in vitro.

Refer to FIG. 14 that compares cross-sections of the intestinal villi regenerated in vitro in the present invention and with the one shown in Yang, Q. et al. (2001) Science 294:2155–8). It is very obvious that at least morphologically the in vitro generated intestinal villi have the same types of cells as the ones identified in a tissue biopsy in this published literature: epithelial cells, goblet cells, Paneth cells, and endocrinal cells.

FIG. 15 shows the comparison of the vertical section of normal villi in a tissue section in a biopsy and the one regenerated in vitro according to the present invention. As shown in FIG. 15, the in vitro generated villi have the same morphology and structure as the ones in the biopsy.

Example 3

Culture of Mouse Bone Marrow Tissue in Vitro

The in vitro experiment on mouse bone marrow was carried out by following this protocol:

Harvested bone marrow cells from Balb/c mouse provided by qualified Laboratory Animal Institute, Chinese Academy of Medical Sciences. The cell collection method is known to skilled artisans in this field. In the test wells, RPMI1640 medium and a mixture of stigmasterol, β-sitosterol and campesterol (1:1:1 in weight, about 1% w/w of the total weight of the medium), beeswax at 10% (w/w medium), and obabenine at 0.003% (w/w medium).

After continuous culture of the bone marrow for 64 days, the following results were obtained. Refer to FIG. 16A. Progenitor cells appeared in the test group, these cells aggregated and formed large and small colonies, and evolved into bone marrow tissues gradually.

Refer to FIG. 16B, after 10 days of continuous culture, bone marrow progenitor cells appeared in the control group. However, after 15th day of culture, the number of fibroblasts increased gradually and no bone marrow tissues formed.

Example 4

Culture of Rat Nerve Tissue in Vitro

An in vitro experiment on rat bone neurons was carried out by following this protocol:

Collected neurons from SD rats provided by qualified Laboratory Animal Institute, Chinese Academy of Medical Sciences. The neuron collection method was known to skilled artisans in this field. In the test wells, the growth medium was L15 medium plus an inventive cell growth regulator (15 g/100 ml medium) which is mixture of stigmasterol, β-sitosterol and campesterol (1:1:1 in weight, about 1% w/w of the total weight of the medium), beeswax of 10% (w/w medium), baicalin of 1% (w/w medium), and berberine of 0.001% (w/w medium). The control well only contained L15 medium.

Figure 17B:
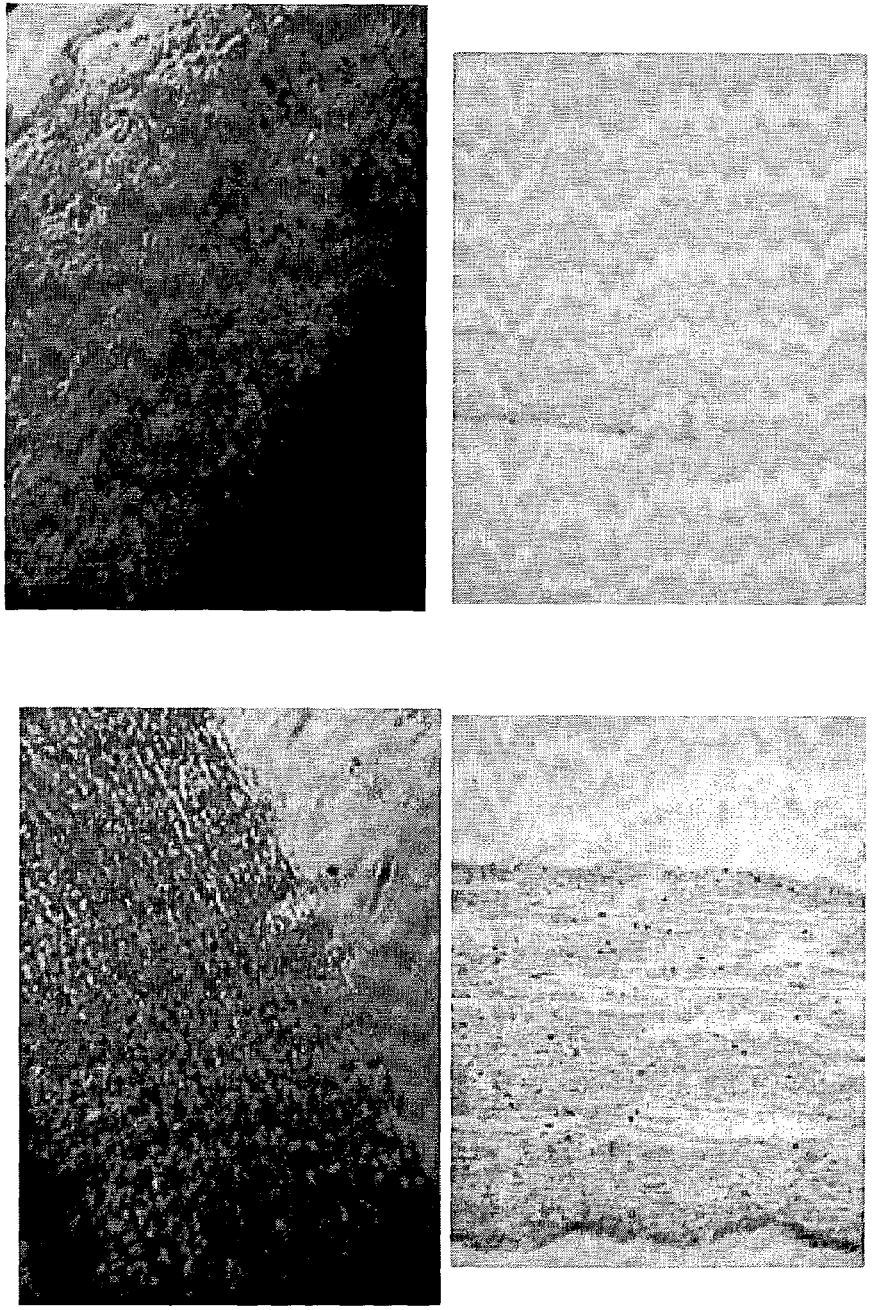
FIG. 17B shows the structure of regenerated nerve tissues in the presence of the inventive composition (upper left panel, its HE stained image shown in the lower left panel) and the structure of degenerated nerve tissue in the absence of the inventive composition (upper right panel, its HE stained image shown in the lower right panel).

After continuous culture for 25 days, the following results were obtained. Refer to FIG. 17A. there was obvious elongation of nerve tissue in test group 1. In contrast, nerve tissue contracted and degenerated in control group 2 (upper pictures in FIG. 17A). Observed microscopically under ×250 magnification, the regenerated nerve tissue in test group 1 appeared with clear grains and in a form of bundle. In contrast, nerve tissue in control group 1 showed obvious degeneration (upper pictures in FIG. 17B). HE staining indicated the same results in test group 2 and test group 1 (lower pictures in FIG. 17B) while nerve tissue in control group 2 showed obvious degeneration (lower pictures in FIG. 17B).

Example 5

Culture of Mouse Pancreatic Cells in Vitro

An in vitro experiment on mouse pancreatic cells was carried out by following this protocol:

Collected pancreatic cells from Kunming mouse provided by qualified Laboratory Animal Institute, Chinese Academy of Medical Sciences. The cell collection method was known to skilled artisans in this field. In the test wells, In the test wells, the growth medium was Ham's F12 medium plus an inventive cell growth regulator (50 g/100 ml medium) which is a mixture of spinasterol, 24-dehydrocholesterol, poriferasterol and daucosterol (1:1:1:1 in weight, about 20% w/w of the total weight of the medium), beeswax at 0.1% (w/w medium), baicalin at 1% (w/w medium), berberine at 0.001% (w/w medium), and narcotoline at 0.001% (w/w medium). The control medium only contained Ham's F12 medium.

Continuously cultured the cells for 40 days. Refer to FIG. 18, pancreatic cells evolved into pancreatic tissues and the tissues further matured after 92 days of culture. In contrast, in the control group a large number of cells died and no pancreatic tissues formed after 55 days of culture. The pancreatic cells were necrotic and died extensively in the control group.

Figure 19:
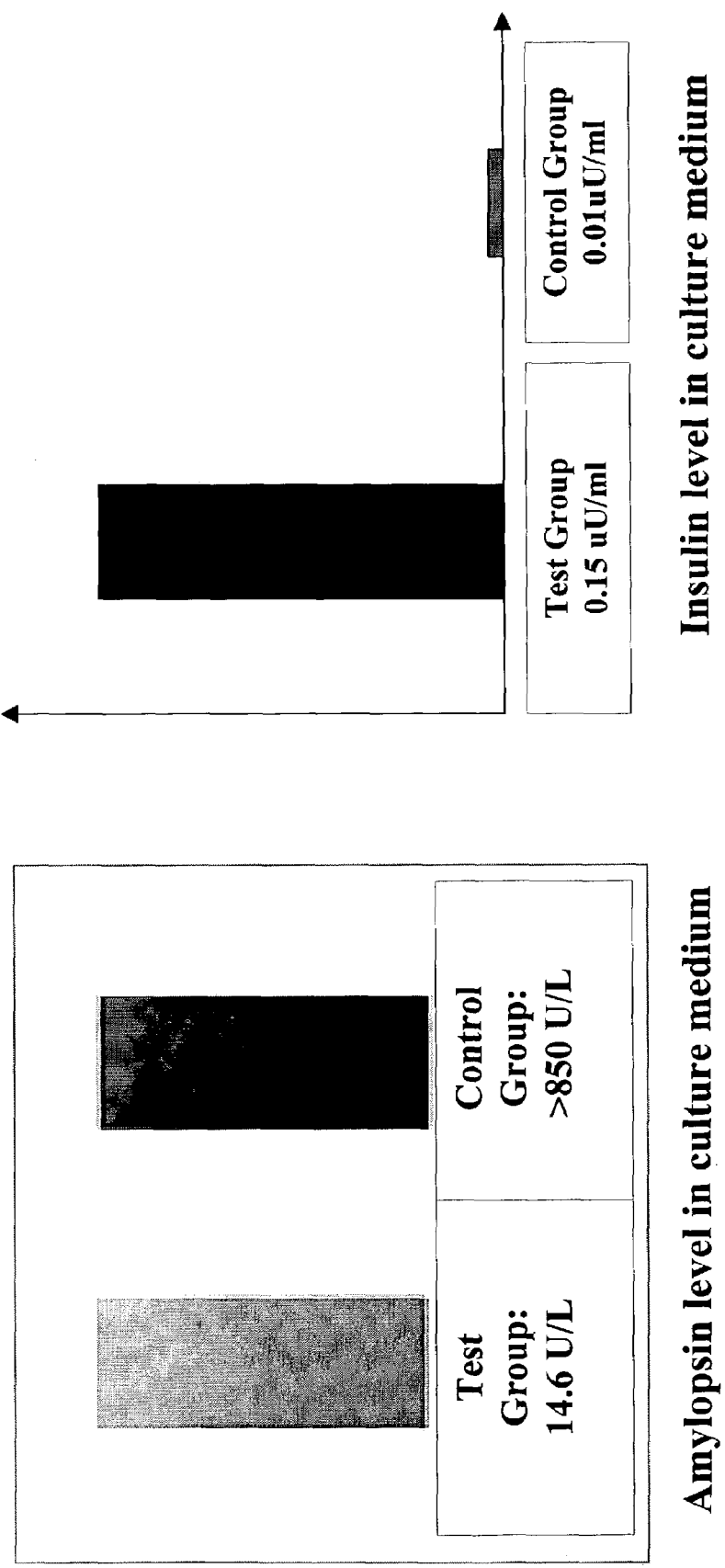
FIG. 19 shows levels of amylopsin (left panel) and insulin (right panel) in the culture medium of pancreatic tissue in the presence and absence of the inventive composition.

To verify the function of pancreatic tissues in the test group, the medium was collected from the wells where the pancreatic cells were cultured for at least 60 days and examined for the levels of the amylopsin and insulin in the medium by using a method known to skilled artisans in the field. The concentration of amylopsin was 14.6 unit/L in the test group and more than 850 unit/L in the control group (left panel, FIG. 19). The concentration of insulin was 0.15 μunit/ml in the test group and 0.01 μunit/ml in the control group (right panel, FIG. 19). The difference between two groups is statistically significant.

Example 6

Culture of Mouse Renal Cells in Vitro

An in vitro experiment on mouse renal cells was carried out by following this protocol:

Collected renal cells from Kunming mice provided by qualified Laboratory Animal Institute, Chinese Academy of Medical Sciences. The cell collection method is known to skilled artisans in this field. In the test wells, the growth medium was MB752/1 medium plus an inventive cell growth regulator (30 g/100 ml medium) which is a mixture of sterol at 0.5% w/w of the total weight of the medium, beeswax at 20% (w/w medium), baicalin at 1% (w/w medium), berberine at 0.001% (w/w medium), narcotoline at 0.001% (w/w medium), and earth worm at 2% (w/w medium). The control medium only contained MB752/1 medium.

Refer to FIG. 20. Through continuous culture of renal cortical cells for 60 days, new nephrons evolved in the test group. These nephrons were very obvious. In contrast, a large number of cells died out in the control group.

Example 7

Culture of Human Hair Follicles in Vitro

An in vitro experiment on human hair follicles was carried out by following this protocol:

Collected hair follicles through depilation of human head hair and body hair. Obtained the follicular cells from the follicular bulge area. In the test wells (24-well plate), the growth medium was 5% FCS MEM medium (2 ml) plus an inventive cell growth regulator (35 g/100 ml medium) which is a mixture of β-sitosterol at 0.5% w/w of the total weight of the medium, beeswax at 20% (w/w medium), baicalin at 1% (w/w medium), berberine at 0.001% (w/w medium), narcotoline at 0.001% (w/w medium), and earth worm at 0.001% (w/w medium). The control medium only contained 5% FCS MEM medium.

Figure 21B:
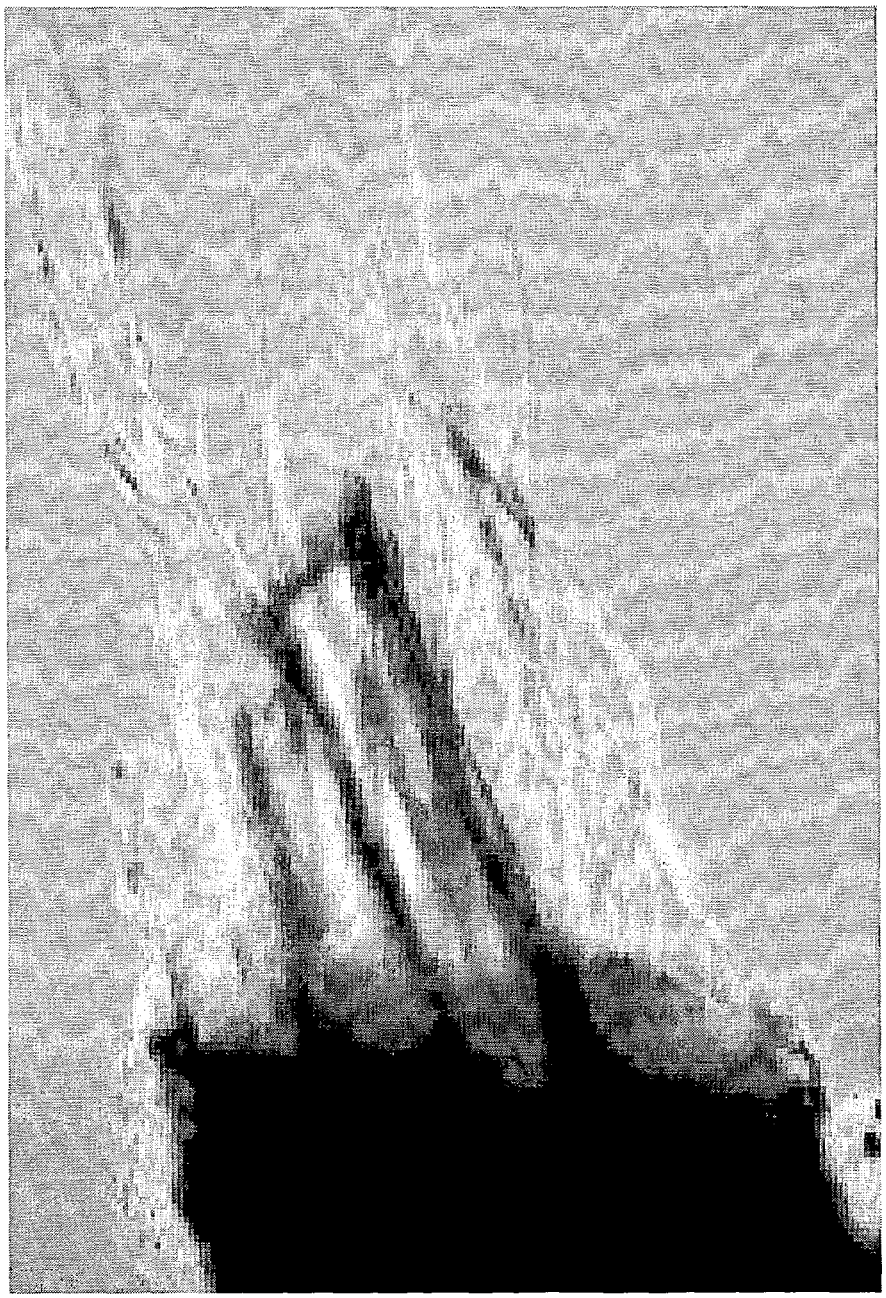
FIG. 21B shows a magnified image of the cloned hair follicle with collagenous fiber growing from the hair follicle.

Follicular cells showed obvious colonization through continuous culture for 70 days. After 78 days of culture, follicular cells attached to each other, formed follicles and further evolved into follicular tissues and tissue-organs (FIG. 21A). Eventually, hair grew out the follicles (FIG. 21B).

Example 8

Culture of Rat Cardiomuscular Cells in Vitro

An in vitro experiment on rat cardiomuscular cells was carried out by following this protocol:

Collected cardiomuscular cells from SD rat provided by qualified Laboratory Animal Institute, Chinese Academy of Medical Sciences. The cell collection method is known to skilled artisans in this field. In the test wells, the growth medium was CMRL1066 medium plus an inventive cell growth regulator (25 g/100 ml medium) which is a mixture of sterol at 6% w/w of the total weight of the medium, beeswax at 20% (w/w medium), baicalin at 10% (w/w medium), obabenine at 0.02% (w/w medium), berberine at 0.01% (w/w medium), narcotoline at 0.01% (w/w medium), and earth worm at 2% (w/w medium). The control medium only contained CMRL1066 medium.

Refer to FIG. 22. Through continuous culture for 48 days, the cardiomuscular cells began to link and cardiomuscular tissues formed after culture for 65 days.

Example 9

Culture of Rat Thymocytes in Vitro

An in vitro experiment on rat thymocytes was carried out by following this protocol:

Collected thymocytes from Wistar rat provided by qualified Laboratory Animal Institute, Chinese Academy of Medical Sciences. The cell collection method is known to skilled artisans in this field. In the test wells, the growth medium was CMRL1066 medium plus an inventive cell growth regulator (40 g/100 ml medium) which is a mixture of stigmasterol, β-sitosterol, chalinosterol, and γ-sitosterol (0.5:1:0.85:0.5, 10% w/w of the total weight of the medium), beeswax at 15% (w/w medium), baicalin at 2% (w/w medium), obabenine at 0.05% (w/w medium), berberine at 0.03% (w/w medium), and earth worm at 0.01% (w/w medium).

Figure 23:
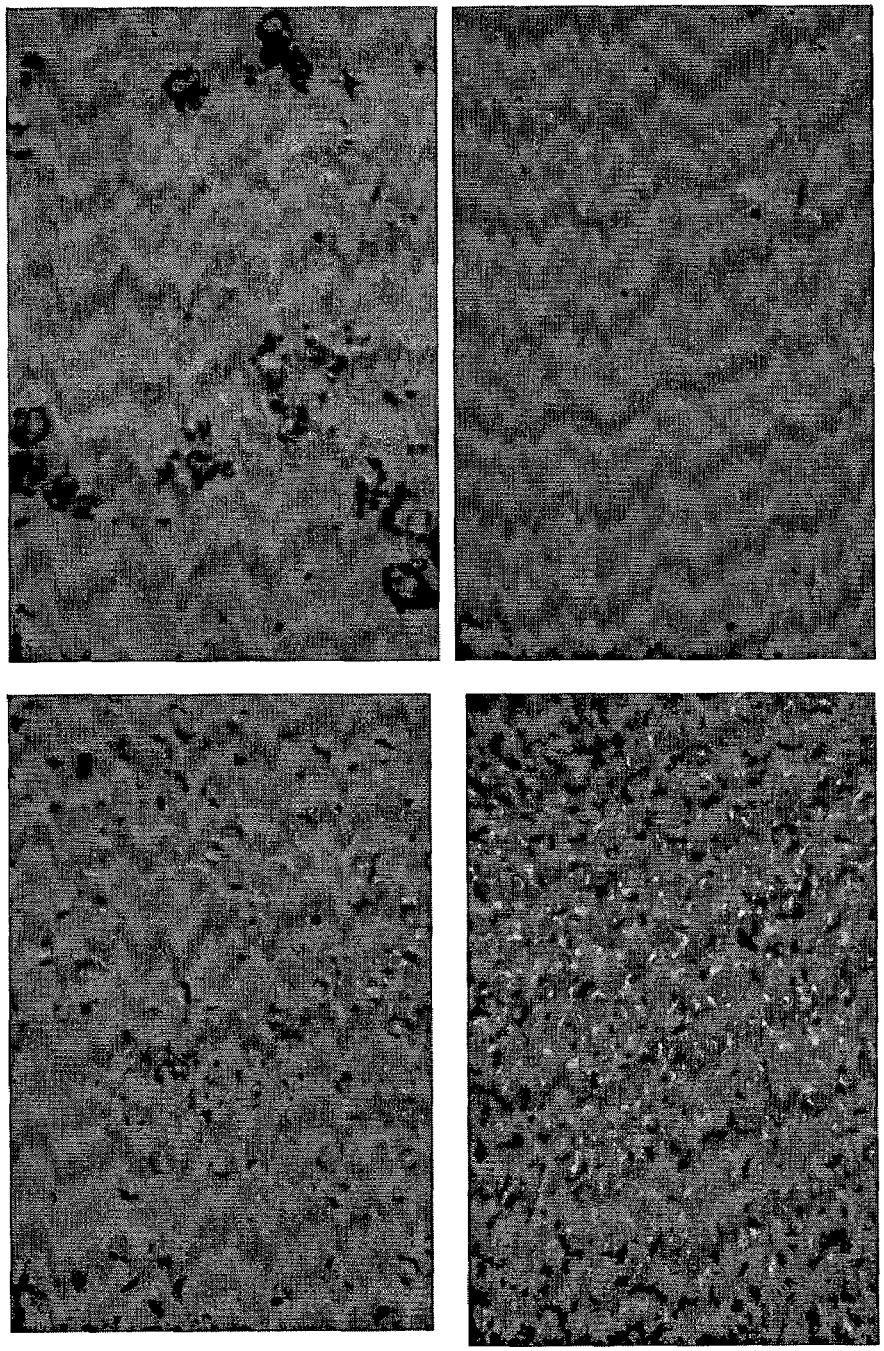
FIG. 23 shows that rat thymocytes (upper left panel) were cultured in vitro to gradually form thymic tissue (moving from the lower left panel to the lower right panel) while thymocytes in the control group died (upper right panel).

Refer to FIG. 23. In the test group, thymocytes began to aggregate and connect after continuous culture for 15 days, and the replication of thymic tissues completed after continuous culture for 34 days. In contrast, thymocytes in the control group began to die after 8 to 10 days of culture, and eventually no thymic tissues formed.

Example 10

Culture of Rat Hepatocytes in Vitro

An in vitro experiment on rat liver cells was carried out by following this protocol:

Collected hepatocytes from Wistar rats provided by qualified Laboratory Animal Institute, Chinese Academy of Medical Sciences. The cell collection method is known to skilled artisans in this field. In the test wells, the growth medium was 15% FCS CMRL1066 medium plus an inventive cell growth regulator (50 g/100 ml medium) which is a mixture of stigmasterol, β-sitosterol, chalinosterol, and γ-sitosterol (0.5:1:0.85:0.5%, 10% w/w of the total weight of the medium), beeswax at 10% (w/w medium), baicalin at 1% (w/w medium), obabenine at 0.05% (w/w medium), berberine at 0.03% (w/w medium), and earth worm at 0.01% (w/w medium).

Figure 24:
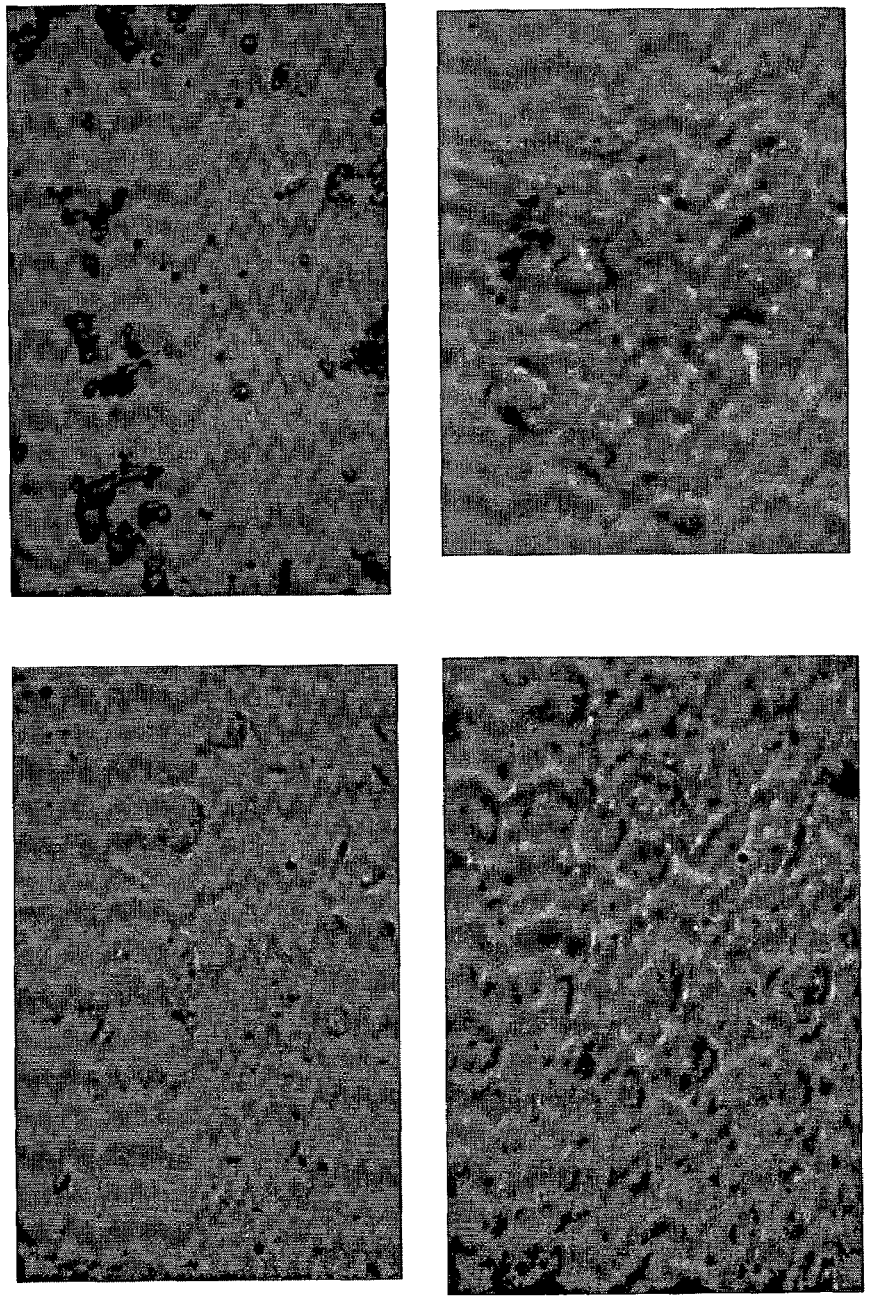
FIG. 24 shows that rat hepatocytes (upper left panel) were cultured in vitro to gradually form hepatic lobules (the lower left panel) and liver tissue (lower right panel) while hepatoytes in the control group died (upper right panel).

Refer to FIG. 24, the liver cells began to proliferate, aggregate and link after continuous culture for 15 days. After culture for 25 days, hepatic lobules appeared and the liver tissue replication completed. In contrast, liver cells in control group began to die after 8 to 10 days of culture and eventually no intact liver tissue formed.

Example 11

Regeneration of Mouse Stomach in Vivo and in Situ

In this example, a mouse model for with acute hemorrhagic gastric ulcer was created by i.g. with ethanol. Afterwards stomachs of mice in the test group were filled with the same cell growth regulator as used in example 2. Three day later, the mice of test and control groups were sacrificed and their stomachs isolated.

FIG. 25 compares the stomachs of the mice in the test and control groups. It is obvious that mucosa damaged by the acute gastric ulcer in the test group were repaired without any scar. In contrast, in the control group, typical hemorrhagic ulcer of mucosa occurred. As shown in the left panel of FIG. 25, the black spots were ulcers and necrosis of mucosa appeared.

Example 12

Regeneration of Human Stomach in Vivo and in Situ

FIG. 26 shows a stomach of a patient with gastroduodenal ulcer, an obvious ulcer could be observed in mucosa of the gastric angular area with mucosa necrotized in omnilayer and peripheral tissues appearing inflammatory. After treatment for ten days with the same cell growth regulator as used in example 2, gastric mucosa in the lesion area were repaired in vivo and in situ with no scar formation as observed by stomachoscopy. The same results were obtained for the peripheral tissues.

Example 13

Regeneration of Plant Tissue in Vivo and in Situ

In this example, a growing winter melon was chosen. Three pieces of thin rinds in 2 cm×2 cm were scraped off with a knife and the wounds on the melon were treated with three different methods within 5 minutes: one smeared with vegetable oil (sesame oil or soy oil), one coated with water-wetted gauze, and the third with nothing. The treatments lasted for ten days, one time per day.

Ten days later, new rind grew in the wound which was smeared with vegetable oil. In contrast, the wound which was coated with water-wetted gauze was rotten, and there was a "scar" in wound treated with nothing.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the substituents, means of preparation and/or methods of use of the invention, may be made without departing from the spirit and scope thereof.

What is claimed is:

1. A method for culturing cells in vitro, comprising:
providing tissue cells or a tissue isolated from a predetermined site of the body of a mammal;
forming a tissue culture medium by adding fatty acid-containing oil in which a sterol compound of at least 0.1%, baicalin of 0.001–2% and wax of 1–20% by weight based on the total weight of the oil are dissolved to a culture medium containing at least 50% of water; and
culturing the isolated tissue cells or tissue in the tissue culture medium.

2. The method of claim 1, wherein the tissue cells or tissue are isolated from a rodent, a primate or a human.

3. The method of claim 1, wherein the tissue cells or tissue are isolated from a fully developed adult human.

4. The method of claim 1, wherein the tissue cells or tissue are isolated from live mammal.

5. The method of claim 1, wherein the isolated tissue cells or tissue are from the brain, heart, liver, lung, intestine, stomach, kidney, bone marrow, or skin of the mammal, excluding embryonic stem cells and the blastocyst of the mammal.

6. The method of claim 1, wherein the tissue is processed in vitro to produce cells which are then isolated and cultured in the tisuue culture medium to produce the tissue-organ.

7. The method of claim 1, wherein the cells contained in the isolated tissue cells or tissue are activated in the tissue culture medium to continuously proliferate and differentiate for at least 5 days.

8. The method of claim 1, wherein the cells contained in the isolated tissue cells or tissue are activated in the tissue culture medium to continuously proliferate and differentiate for at least 30 days.

9. The method of claim 1, wherein the cells contained in the isolated tissue cells or tissue are activated in culture medium to continuously proliferate and differentiate for at least 50 days.

10. The method of claim 1, wherein the oil comprises vegetable oil or animal oil.

11. The method of claim 1, wherein the oil comprises an oil selected from the group consisting of corn oil, peanut oil, cottonseed oil, rice bran oil, safflower oil, tea tree oil, pine nut oil, macadamia nut oil, camellia seed oil, rose hip oil, sesame oil, olive oil, soybean oil and combinations thereof.

12. The method of claim 1, wherein the oil comprises sesame oil.

13. The method of claim 1, wherein the fatty-acid is selected from the group consisting of palmitic acid, linoleic acid, oleic acid, trans-oleic acid, stearic acid, arachidic acid, and tetracosanoic acid.

14. The method of claim 1, wherein the sterol compound is an animal sterol or a plant sterol.

15. The method of claim 1, wherein the sterol compound is selected from the group consisting of stigmasterol, campesterol, β-sitosterol, chalinosterol, clionasterol, brassicasterol, α-spinasterol, daucosterol, avenasterol, cycloartenol, desmosterol, and poriferasterol.

16. The method of claim 1, wherein the sterol compound is a combination of stigmasterol, β-sitosterol, and campesterol.

17. The method of claim 1, wherein the sterol compound is a combination of stigmasterol and β-sitosterol.

18. The method of claim 1, wherein the sterol compound is a combination of bras sicasterol and β-sitosterol.

19. The method of claim 1, wherein the sterol compound is a combination of brassicasterol, stigmasterol and β-sitosterol.

20. The method of claim 1, wherein the wax is edible wax.

21. The method of claim 1, wherein the wax is selected from the group consisting of beeswax, castorwax, glycowax, and carnaubawax.

22. The method of claim 1, wherein the wax is beeswax.

23. The method of claim 1, wherein the concentration of baicalin is about 0.02–0.5% by weight based on the total weight of the oil.

* * * * *